US006726705B2

(12) United States Patent
Peterson et al.

(10) Patent No.: US 6,726,705 B2
(45) Date of Patent: Apr. 27, 2004

(54) MECHANICAL METHOD AND APPARATUS FOR BILATERAL TISSUE FASTENING

(75) Inventors: James A. Peterson, Edina, MN (US); Christopher J. Sperry, Plymouth, MN (US); Joseph M. Gryskiewicz, Edina, MN (US); Delmer L. Smith, Edina, MN (US)

(73) Assignee: Incisive Surgical, Inc., Minnetonka, MN (US)

( * ) Notice: Subject to any disclaimer, the term of this patent is extended or adjusted under 35 U.S.C. 154(b) by 187 days.

(21) Appl. No.: 10/179,628

(22) Filed: Jun. 25, 2002

(65) Prior Publication Data

US 2003/0236550 A1 Dec. 25, 2003

(51) Int. Cl.[7] .................................................. A61B 1/00
(52) U.S. Cl. ......................................................... 606/216
(58) Field of Search .......................... 606/75, 205, 213, 606/219, 220, 221, 215, 216, 142, 143, 139; 227/19, 155, 175.1; 128/898

(56) References Cited

U.S. PATENT DOCUMENTS

| | | | |
|---|---|---|---|
| 2,351,608 | A | 6/1944 | Greenwood |
| 2,439,383 | A | 4/1948 | Erickson |
| 2,526,902 | A | 10/1950 | Rublee |
| 2,881,762 | A | 4/1959 | Lowrie |
| 2,959,172 | A | 11/1960 | Held |
| 3,082,426 | A | 3/1963 | Miles |
| 3,123,077 | A | 3/1964 | Alcamo |
| 3,297,033 | A | 1/1967 | Schmitt et al. |
| 3,344,790 | A | 10/1967 | Dorner |
| 3,636,956 | A | 1/1972 | Schneider |
| 3,643,851 | A | 2/1972 | Green et al. |
| 3,716,058 | A | 2/1973 | Tanner, Jr. |
| 3,757,629 | A | 9/1973 | Schneider |
| 3,792,010 | A | 2/1974 | Wasserman et al. |
| 4,014,492 | A | 3/1977 | Rothfuss |
| 4,027,676 | A | 6/1977 | Mattei |
| 4,047,533 | A | 9/1977 | Perciaccante et al. |
| 4,162,678 | A | 7/1979 | Fedotov et al. |

(List continued on next page.)

OTHER PUBLICATIONS

Brochure: *Information Booklet for Auto Suture® Purse String Instrument*, Auto Suture Company, a division of United States Surgical Corporation, Norwalk, CT, 2 pgs., 1978.

Brochure: *La Sutura Perde il Filo*, Farmitalia Carlo Erba, 4 pgs., not dated.

*Evaluation of New Absorbable Lactomer Subcuticular Staple*, G.C. Zachmann, P.A. Foresman, T.J. Bill, D.J. Bentrem, G.T. Rodeheaver, R.F. Edlich, Journal of Applied Biomaterial, vol. 5, No. 3, pp. 221–116, 1994.

*Primary Examiner*—Julian W. Woo
*Assistant Examiner*—P Roberts
(74) *Attorney, Agent, or Firm*—Patterson, Thuente, Skaar & Christensen, P.A.

(57) ABSTRACT

A mechanical system for bilaterally securing skin tissue preferably utilizes a tissue manipulator apparatus to approximate a portion of an interior surface of each of two pieces of living dermis tissue along a vertical interface below an exterior surface without overlapping either interior surface across the vertical interface. An applicator apparatus includes a driving head portion positioned in the vertical interface and at least partially below the exterior surface and a handle portion positioned at least partially above the exterior surface. The applicator apparatus bilaterally drives at least one portion of the fastener through each piece of the living dermis tissue behind the interior surface of that piece of tissue such that the fastener is positioned below the exterior surface and a portion of the fastener is positioned generally transverse to the vertical interface.

10 Claims, 22 Drawing Sheets

U.S. PATENT DOCUMENTS

| | | | | | |
|---|---|---|---|---|---|
| 4,259,959 | A | | 4/1981 | Walker | |
| 4,261,244 | A | | 4/1981 | Becht et al. | |
| 4,317,451 | A | | 3/1982 | Cerwin et al. | |
| 4,399,810 | A | | 8/1983 | Samuels et al. | |
| 4,407,286 | A | | 10/1983 | Noiles et al. | |
| 4,410,125 | A | | 10/1983 | Noiles et al. | |
| 4,428,376 | A | * | 1/1984 | Mericle | 606/219 |
| 4,485,816 | A | | 12/1984 | Krumme | |
| 4,493,322 | A | | 1/1985 | Becht | |
| 4,505,273 | A | | 3/1985 | Braun et al. | |
| 4,506,669 | A | | 3/1985 | Blake, III | |
| 4,508,253 | A | | 4/1985 | Green | |
| 4,526,173 | A | | 7/1985 | Sheehan | |
| 4,526,174 | A | | 7/1985 | Froehlich | |
| 4,535,772 | A | | 8/1985 | Sheehan | |
| 4,557,265 | A | | 12/1985 | Andersson | |
| 4,566,620 | A | | 1/1986 | Green et al. | |
| 4,568,009 | A | | 2/1986 | Green | |
| 4,570,623 | A | | 2/1986 | Ellison et al. | |
| 4,573,622 | A | | 3/1986 | Green et al. | |
| 4,583,670 | A | | 4/1986 | Alvarado | |
| 4,592,498 | A | | 6/1986 | Braun et al. | |
| 4,593,843 | A | | 6/1986 | Saravis | |
| 4,596,350 | A | | 6/1986 | Smith et al. | |
| 4,618,086 | A | | 10/1986 | Li et al. | |
| 4,665,916 | A | | 5/1987 | Green | |
| 4,719,917 | A | | 1/1988 | Barrows et al. | |
| 4,728,020 | A | | 3/1988 | Green et al. | |
| 4,741,337 | A | | 5/1988 | Smith et al. | |
| 4,752,024 | A | | 6/1988 | Green et al. | |
| 4,753,636 | A | | 6/1988 | Free | |
| 4,762,260 | A | | 8/1988 | Richards et al. | |
| 4,776,506 | A | | 10/1988 | Green | |
| 4,789,090 | A | | 12/1988 | Blake, III | |
| 4,895,148 | A | | 1/1990 | Bays et al. | |
| 4,899,745 | A | | 2/1990 | Laboureau et al. | |
| 4,915,100 | A | | 4/1990 | Green | |
| 4,924,866 | A | | 5/1990 | Yoon | |
| 4,969,591 | A | | 11/1990 | Richards et al. | |
| 4,976,686 | A | | 12/1990 | Ball et al. | |
| 4,994,073 | A | | 2/1991 | Green | |
| 5,002,562 | A | | 3/1991 | Oberlander | |
| 5,007,921 | A | | 4/1991 | Brown | |
| 5,015,252 | A | * | 5/1991 | Jones | 606/205 |
| 5,035,692 | A | | 7/1991 | Lyon et al. | |
| 5,044,540 | A | | 9/1991 | Dulebohn | |
| 5,047,047 | A | | 9/1991 | Yoon | |
| 5,062,563 | A | | 11/1991 | Green et al. | |
| 5,078,731 | A | | 1/1992 | Hayhurst | |
| 5,089,009 | A | | 2/1992 | Green | |
| 5,108,422 | A | | 4/1992 | Green et al. | |
| 5,129,570 | A | | 7/1992 | Schulze et al. | |
| 5,156,609 | A | | 10/1992 | Nakao et al. | |
| 5,158,566 | A | | 10/1992 | Pianetti | |
| 5,158,567 | A | | 10/1992 | Green | |
| 5,160,339 | A | | 11/1992 | Chen et al. | |
| 5,236,440 | A | * | 8/1993 | Hlavacek | 606/219 |
| 5,257,713 | A | | 11/1993 | Green et al. | |
| 5,258,009 | A | | 11/1993 | Conners | |
| 5,258,010 | A | | 11/1993 | Green et al. | |
| 5,269,783 | A | | 12/1993 | Sander | |
| 5,269,792 | A | | 12/1993 | Kovac et al. | |
| 5,285,944 | A | | 2/1994 | Green et al. | |
| 5,292,326 | A | | 3/1994 | Green et al. | |
| 5,297,714 | A | | 3/1994 | Kramer | |
| 5,324,307 | A | | 6/1994 | Jarrett et al. | |
| 5,337,937 | A | | 8/1994 | Remiszewski et al. | |
| 5,342,376 | A | * | 8/1994 | Ruff | 606/151 |
| 5,366,134 | A | | 11/1994 | Green et al. | |
| 5,389,102 | A | | 2/1995 | Green et al. | |
| 5,392,979 | A | | 2/1995 | Green et al. | |
| 5,398,861 | A | | 3/1995 | Green | |
| D357,316 | S | | 4/1995 | Green et al. | |
| 5,413,584 | A | | 5/1995 | Schulze | |
| 5,423,856 | A | | 6/1995 | Green | |
| 5,425,489 | A | | 6/1995 | Shichman et al. | |
| 5,425,747 | A | | 6/1995 | Brotz | |
| 5,456,401 | A | | 10/1995 | Green et al. | |
| 5,478,003 | A | | 12/1995 | Green et al. | |
| 5,480,089 | A | | 1/1996 | Blewett | |
| 5,482,197 | A | | 1/1996 | Green et al. | |
| 5,489,058 | A | | 2/1996 | Plyley et al. | |
| 5,489,287 | A | | 2/1996 | Green et al. | |
| 5,509,596 | A | | 4/1996 | Green et al. | |
| 5,514,149 | A | | 5/1996 | Green et al. | |
| 5,549,619 | A | | 8/1996 | Peters et al. | |
| 5,551,622 | A | | 9/1996 | Yoon | |
| 5,558,266 | A | | 9/1996 | Green et al. | |
| 5,562,241 | A | | 10/1996 | Knodel et al. | |
| 5,571,285 | A | | 11/1996 | Chow et al. | |
| 5,573,541 | A | | 11/1996 | Green et al. | |
| 5,579,978 | A | | 12/1996 | Green et al. | |
| 5,584,859 | A | * | 12/1996 | Brotz | 606/228 |
| 5,591,178 | A | | 1/1997 | Green et al. | |
| 5,593,423 | A | | 1/1997 | Person et al. | |
| 5,618,311 | A | | 4/1997 | Gryskiewicz | |
| 5,658,312 | A | | 8/1997 | Green et al. | |
| 5,662,258 | A | | 9/1997 | Knodel et al. | |
| 5,706,997 | A | | 1/1998 | Green et al. | |
| 5,725,538 | A | | 3/1998 | Green et al. | |
| 5,728,108 | A | | 3/1998 | Griffiths et al. | |
| 5,794,834 | A | | 8/1998 | Hamblin et al. | |
| 5,816,471 | A | | 10/1998 | Plyley et al. | |
| 5,829,662 | A | | 11/1998 | Allen et al. | |
| 5,871,135 | A | | 2/1999 | Williamson, IV et al. | |
| 5,878,937 | A | | 3/1999 | Green et al. | |
| 5,902,319 | A | | 5/1999 | Daley | |
| 5,976,160 | A | | 11/1999 | Crainich | |
| 5,984,949 | A | | 11/1999 | Levin | |
| 6,090,131 | A | | 7/2000 | Daley | |
| 6,120,526 | A | | 9/2000 | Daley | |
| 6,131,789 | A | | 10/2000 | Schulze et al. | |
| 6,159,224 | A | | 12/2000 | Yoon | |
| 6,250,532 | B1 | | 6/2001 | Green et al. | |
| 6,270,517 | B1 | * | 8/2001 | Brotz | 606/228 |
| 6,387,104 | B1 | * | 5/2002 | Pugsley et al. | 606/139 |

* cited by examiner

MECHANICAL METHOD AND APPARATUS FOR BILATERAL TISSUE FASTENING

FIELD OF THE INVENTION

The present invention relates generally to the field of surgical instruments such as surgical staplers, clip applicators and sutureless closure devices. More particularly, the present invention relates to a mechanical method and apparatus for fastening tissue, such as skin tissue, with a fastener positioned below the tissue surface that bilaterally secures opposed pieces of tissue.

BACKGROUND OF THE INVENTION

When an opening in tissue is created either through an intentional incision or an accidental wound or laceration, biological healing of the opening commences through the proximity of the opposed living tissue surfaces. If the opening is very large or if its location subjects the wound to continual movement, a physician will seek to forcibly hold the sides of the opening in close proximity so as to promote the healing process.

In the case of skin tissue, for example, healing occurs best when the opposing dermal layers of the skin tissue are held in proximity with each other. Human skin tissue is comprised of three distinct layers of tissue. The epidermal layer, also known as the epidermis, is the outermost layer and includes non-living tissue cells. The dermal layer, or dermis, is the middle layer directly below the epidermal layer and comprises the living tissue of the skin that is the strongest of the three layers. The subcutaneous, or hypodermis layer is the bottom layer of skin tissue and includes less connective tissue making this the weakest layer of skin tissue.

The most prevalent method for forcibly closing a tissue opening is through the use of a suture or "stitches." As early as the second century, the Greeks were using sutures to physically close skin openings. In its simplest form, a suture is simply a length of material that is attached to a tissue-piercing device, such as a needle, and looped through the opposing sides of an opening. The suture is then pulled tight and the loop closes causing the opposing sides of the tissue to come into close physical proximity. The suture loop is held tight by the tying of a knot or some other locking mechanism. The first sutures were made of animal gut. Eventually other natural suture materials including leather, horsehair, flax, cotton and silk came into use.

As the sciences of medical and materials technology have advanced over the course of the past century, new bioabsorbable materials have been developed to further improve upon the basic suturing concept. Examples of modem improvements to the suturing process include enhancements to the suturing apparatus as shown, for example, in U.S. Pat. Nos. 2,439,383, 2,959,172 and 3,344,790, as well as advances in sutures and suture materials as shown, for example, in U.S. Pat. Nos. 3,123,077, 3,297,033, 3,636,956, 3,792,010 4,027,676 and 4,047,533.

While traditional suturing remains a popular method of effectuating closure of skin openings, the use of staples and staplers as a skin closure technique has become increasingly popular, especially in surgical settings where the opening is created through a purposeful incision. In these settings, the incision tends to make a clean, straight cut with the opposing sides of the incision having consistent and non-jagged surfaces. Typically, stapling of a skin opening, for example, is accomplished by manually approximating the opposing sides of the skin opening and then positioning the stapler so that a staple will span the opening. The stapler is then manipulated such that the staple is driven into the skin with one leg being driven into each side of the skin and the cross-member of the staple extending across the opening external to the skin surface. Generally, the legs of the staple are driven into an anvil causing the staple to deform so as to retain the skin tissue in a compressed manner within the staple. This process can be repeated along the length of the opening such that the entire incision is held closed during the healing process.

Much work has been devoted to improving upon the basic stapling process. Developments have gone in a variety of directions and include work devoted to the stapling apparatus as shown, for example, in U.S. Pat. Nos. 3,082,426, 3,643,851, 4,410,125, 4,493,322, 4,592,498, 4,618,086, 4,776,506, 4,915,100, 5,044,540, 5,129,570, 5,285,944, 5,392,979, 5,489,058, 5,551,622, 5,662,258, 5,794,834, 5,816,471, 6,131,789 and 6,250,532. In addition to the stapling apparatus, developments have also been made in the staple design as shown, for example, in U.S. Pat. Nos. 2,351,608, 2,526,902, 2,881,762, 3,757,629, 4,014,492, 4,261,244, 4,317,451, 4,407,286, 4,428,376, 4,485,816, 4,505,273, 4,526,174, 4,570,623, 4,719,917, 4,741,337, 5,007,921, 5,158,567, 5,258,009, 5,297,714, 5,324,307, 5,413,584, 5,505,363 and 5,571,285.

While modern suturing and stapling techniques continue to provide an effective manner of effectuating skin closure, there remains a series of inherent disadvantages in using either of these techniques. The standard technique for both suturing and stapling includes puncturing both the epidermis and dermis. This can result in a wound closure having an unaesthetically pleasing appearance on the surface of the skin. The presence of the fastener exposed through the skin surface provides an opportunity for infection and for accidentally catching the fastener and tearing the wound open. In the case of non-absorbable fasteners, further action by a medical professional is necessary in order to remove the fastener once biological healing is complete.

In order to overcome these limitations, practitioners have developed a number of specialized suturing techniques where the suture is passed only through the dermis effectively positioning the suture below the skin surface, or in a subcuticular fashion. A surgeon has the choice of placing individual or interrupted sutures along the length of an opening. Another suturing option is for the surgeon to use a single strand of suture material to place a plurality of continuing suture loops or running sutures along the length of an opening. While the presence of the suture below the surface can improve the aesthetic nature of the closure, it requires greater skill and technique to accomplish effectively and takes longer than conventional external suturing.

While there has been active development of dermal layer suturing techniques, little has been done in the area of staples and staplers for use in connection with the dermal layer. In a series of patents issued to Green et al., including U.S. Pat. Nos. 5,292,326, 5,389,102, 5,489,287 and 5,573,541, a subcuticular stapling method and apparatus are disclosed that were ultimately commercialized as the US Surgical SQS Subcuticular Stapling Apparatus. The Green et al. patents describe a stapling technique employing a handheld apparatus with jaws to proximate, interdigitate and overlap opposing sides of dermal layer tissue along the length of a skin opening. The apparatus then drives a single spike through the interdigitated and overlapped dermal layers of the opposing skin surfaces in order to secure both sides of the dermal tissue on the single spike. Although this technique reduced the time required to effectuate a subcuticular skin closure, the SQS device was not commercially successful in part because the resulting closure produced an undesirable wave-like scar that sometimes did not heal effectively.

While many improvements have been made to mechanical tissue closure techniques, it would be desirable to provide a mechanical tissue closure system that is capable of effectively delivering fasteners below the skin surface so as to produce an efficient and efficacious tissue closure.

SUMMARY OF THE INVENTION

The present invention is a mechanical system for bilaterally securing skin tissue. Preferably, a tissue manipulator is used to approximate a portion of an interior surface of each of two pieces of living dermis tissue along a vertical interface below an exterior surface without overlapping either interior surface across the vertical interface. An applicator apparatus includes a driving head portion positioned in the vertical interface and at least partially below the exterior surface, and a handle portion positioned at least partially above the exterior surface. The applicator apparatus bilaterally drives at least one portion of the fastener through each piece of the living dermis tissue behind the interior surface of that piece of tissue such that the fastener is positioned below the exterior surface and a portion of the fastener is positioned generally transverse to the vertical interface.

Unlike existing mechanical tissue fastening systems, the present invention recognizes the need for and advantages of a fastener system that captures and retains dermal tissue in a compressed state within a preferably bioabsorbable fastener that is not inserted through the epidermal skin layer. The mechanical fastening system of the present invention is able to consistently and repeatedly interface a fastener with a target tissue zone in the dermal layer such that the fastener inserted into the target tissue zone produces an effective and aesthetically pleasing closure of a tissue opening.

DETAILED DESCRIPTION OF THE PREFERRED EMBODIMENTS

Figure 1:
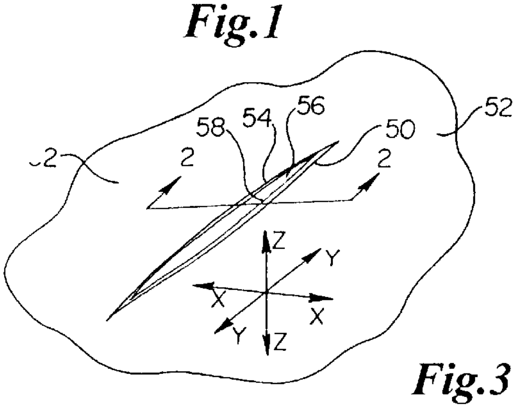
FIG. 1 shows a typical opening in skin tissue such as may be closed by the present invention.
Figure 2:
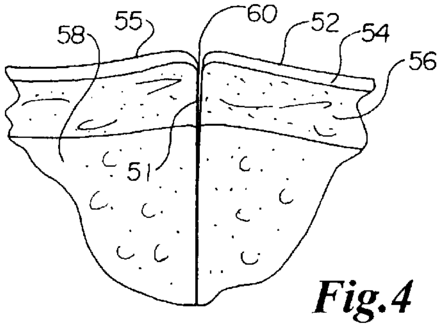
FIG. 2 shows a cross-sectional view of the skin tissue and opening of FIG. 1.
Figure 3:
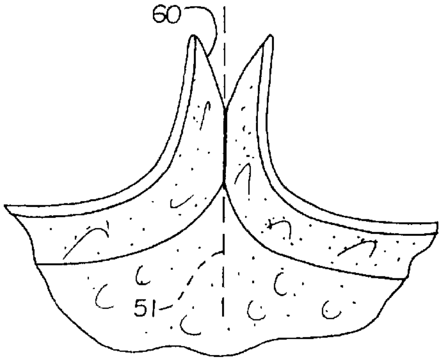
FIG. 3 shows a cross-sectional view of everted skin tissue.

In FIGS. 1–3 there is shown a depiction of a typical opening 50 in the surface of skin 52, such as may be made, for example, by a surgical incision or a wound. As illustrated in FIG. 1, for purposes of describing the present invention, opening 50 may be described as having a length or longitudinal orientation parallel to the y-y axis, a width orientation parallel to the x-x axis, and a depth orientation parallel to the z-z axis. The x-y-z axis for purposes of the present invention is defined with respect to an external tissue surface, which in the case of skin 52 is the outer surface. References to a vertical and horizontal planar orientation in connection with the present invention are made with respect to the external tissue surface at the site of the opening in question. The vertical inner surfaces 60 formed by each side of the opening 50 can be visualized as meeting along a generally vertical interface 51. It will be understood that in the case of an opening that extends over a curved tissue surface, the corresponding horizontal and vertical surfaces associated with the opening will be defined with respect to such curved tissue surface. It also will be understood that the vertical interface 51 may be vertical in only one orientation with respect to the tissue surface, such as in the case when an angled incision has formed the opening 50.

As is best illustrated in the sectional views of FIGS. 2 and 3, human skin 52 generally has three discrete layers. These layers comprise an epidermal layer 54 of mostly non-living tissue having an exterior surface 55, a dermal layer 56 of mostly living tissue, and a subcutaneous tissue layer 58. Although the preferred embodiment of the present invention will be described with respect to human skin tissue 52, it will be understood that the present invention is applicable to closure of openings in other types of tissue having generally defined surfaces, such as fascia, membranes organs, vessels, vasculature, vascular pedicles, skin grafts, bladder and other biocompatible materials with generally defined surfaces such as artificial skin, artificial membranes and synthetic mesh.

It has long been known that the most rapid healing of a skin opening with a minimum of scarring occurs when the inner surfaces 60 of the living dermal layer 56 at each side of the vertical interface 51 of skin opening 50 are brought together and held in close contact in what is referred to as an everted position as is shown in exaggerated fashion in FIG. 3. To the extent that the primarily non-living material of epidermal layer 54 can be excluded from the healing opening, the rapidity and level of scar tissue formed during the healing process will be improved.

Figure 30:
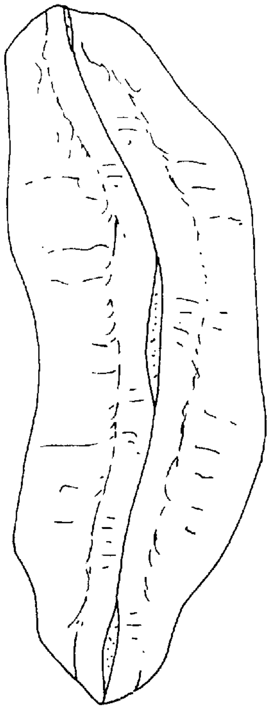
FIG. 30 is a pictorial representation of a skin opening closed with conventional subcutaneous sutures.
Figure 31:
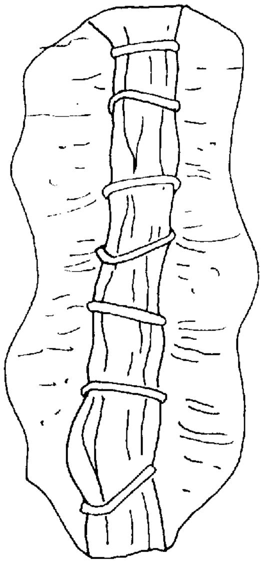
FIG. 31 is a pictorial representation of a skin opening closed by conventional surgical stapling.
Figure 32:
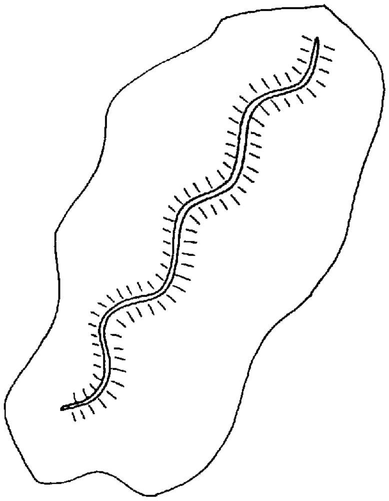
FIG. 32 is a pictorial representation of an opening closed with the prior art interdigitated subcuticular stapler.

The ability of the present invention to provide a more effective and efficacious tissue closure can be seen with reference to FIGS. 30–33, which show skin openings closed by various prior art methods as compared with an opening closed using the bilateral fastening techniques of the present invention. In FIG. 30, there is shown a skin opening closed with subcutaneous sutures. The generally everted condition of the closed opening can produce unattractive scarring and less than optimal healing if the eversion is excessive or inadequate. As can be seen from FIG. 30, obtaining consistency from suture to suture is difficult and the quality of the closure is highly dependent upon the skill of the surgeon. FIG. 31 shows a skin opening closed by conventional surgical stapling. In addition to the generally unattractive appearance of the closed opening, staple openings and the excessive everted condition of the opening may lead to undesirable scarring. In addition, if non-resorbable staples are used, the staples must be removed before complete healing can occur. FIG. 32 shows a depiction of an opening closed with the interdigitated subcuticular stapler known as the SQS device that is described, for example, in U.S. Pat. Nos. 5,292,326, 5,389,102, 5,489,287 and 5,573,541. The characteristic undulating appearance caused by the overlapping interdigitation of the skin may lead to an unusual appearing scar in the healed opening. The overlapping and interdigitation of the skin can also cause epidermis tissue to be interposed between dermal layers, thereby leading to incomplete healing or excessive scarring.

Figure 33:
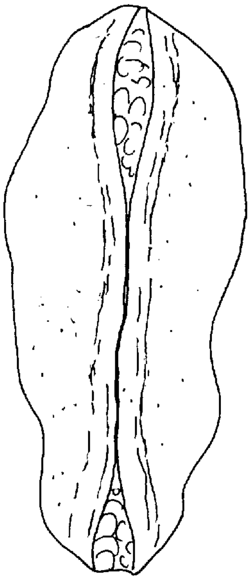
FIG. 33 is a pictorial representation of an opening closed using the bilateral fastening technique of the present invention.

By comparison, an opening that has been partially closed by the method and using the apparatus of the present invention is shown in FIG. 33. As shown, the closed portion of the opening is tightly closed, yet lies flat without undue eversion of the opening leading to better healing performance with minimal scarring. There is consistency in the closure from fastener to fastener. Because the fasteners are positioned below the skin surface (i.e., subcuticular), the fasteners are not exposed and there is no puncturing or button holing of the epidermis that can lead to the increased possibility of infection or interference with the normal healing process. In addition, if fasteners made of a bioresorbable, bioabsorbable or even a bioerodible material are used, there is no need to later remove the fasteners.

The advantages of the present invention are accomplished by an apparatus and method that bilaterally engages target tissue zones 70 on each side of a skin opening 50 with a fastener that is preferably made of a bioresorbable material. As used in connection with the present invention, the term bilateral refers to at least two axis of insertion for a fastener that are on separate sides of the vertical interface 51 of an opening 50. The bilateral engagement may be made either simultaneously or sequentially, and the fastener used may have a variety of configurations and be oriented in a variety of ways as will be further described herein. The location, geometry and orientation of the fastener and the dermal layers in relation to the mechanical apparatus of the present invention are all important considerations to obtaining the most optimal contact and compression of the dermal layer for efficacious closing of the opening. While the skin opening 50 will be described in connection with an opening in a single piece of tissue, it will be understood that the opening 50 could also be between two separate and otherwise unconnected pieces of tissue, or even between a piece of tissue and a piece of biocompatible material to be secured to that piece of tissue.

Figure 4:
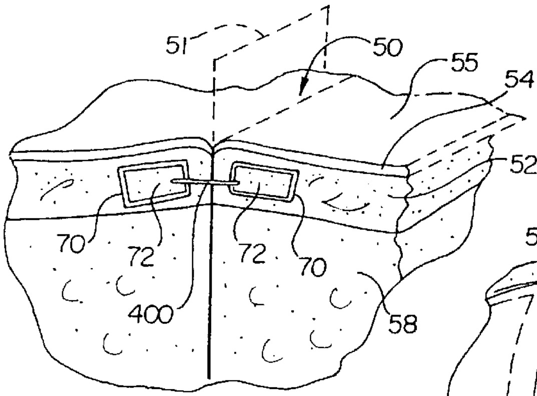
FIG. 4 shows a perspective cross-sectional view of an opening in skin tissue at rest, indicating optimal bilateral target tissue zones.
Figure 5:
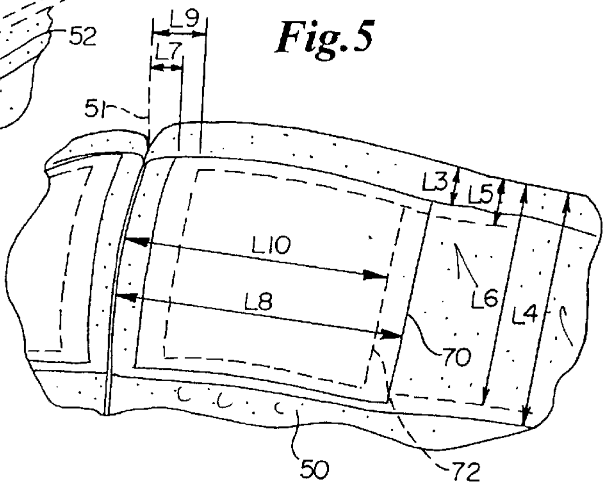
FIG. 5 shows an enlarged view of a target tissue zone.

As is shown in FIGS. 4 and 5, there exists an optimal target tissue zone 70 on each side of vertical interface 51 that may be bilaterally engaged by a fastener in order to achieve optimal dermal contact for healing. This target tissue zone 70 lies within the dermal layer 56, and can be visualized as a rectangular cross-sectional area when the tissue is in a relaxed condition as shown best in FIG. 4. In addition, within target tissue zone 70, there exists a most preferred area 72 for tissue engagement. In the depth orientation, target tissue zone 70 lays between a distance L3 of about 0.1 mm below the surface 55 of epidermal layer 54, and a distance L4 up to 2.0 mm below the surface 55. The most preferred area 72 lies between a distance L5 of about 0.2 mm and a distance L6 of about 0.8 mm below the surface. In the width orientation, target tissue zone 70 lies between a distance L7 of about 1.0 mm and a distance L8 of about 20.0 mm from vertical interface 51. Most preferred area 72 lies between a distance L9 of about 2.0 mm and a distance of about 8.0 mm from vertical interface 51. Because the target tissue zone 70 is not visible to an operator, the manipulator assembly 400 and applicator assembly 100 are preferably designed to consistently and repeatedly enable the operator to position the target tissue zone 70 for deployment of a fastener 400.

Figure 6:
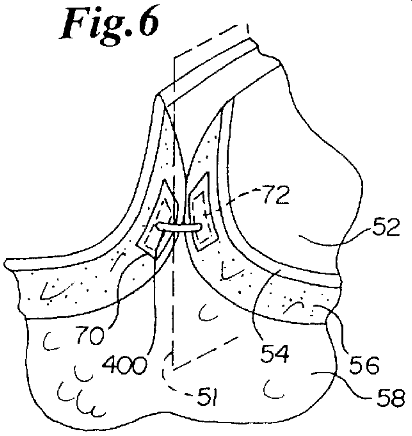
FIG. 6 shows the view of FIG. 4 with the skin tissue everted.
Figure 7:
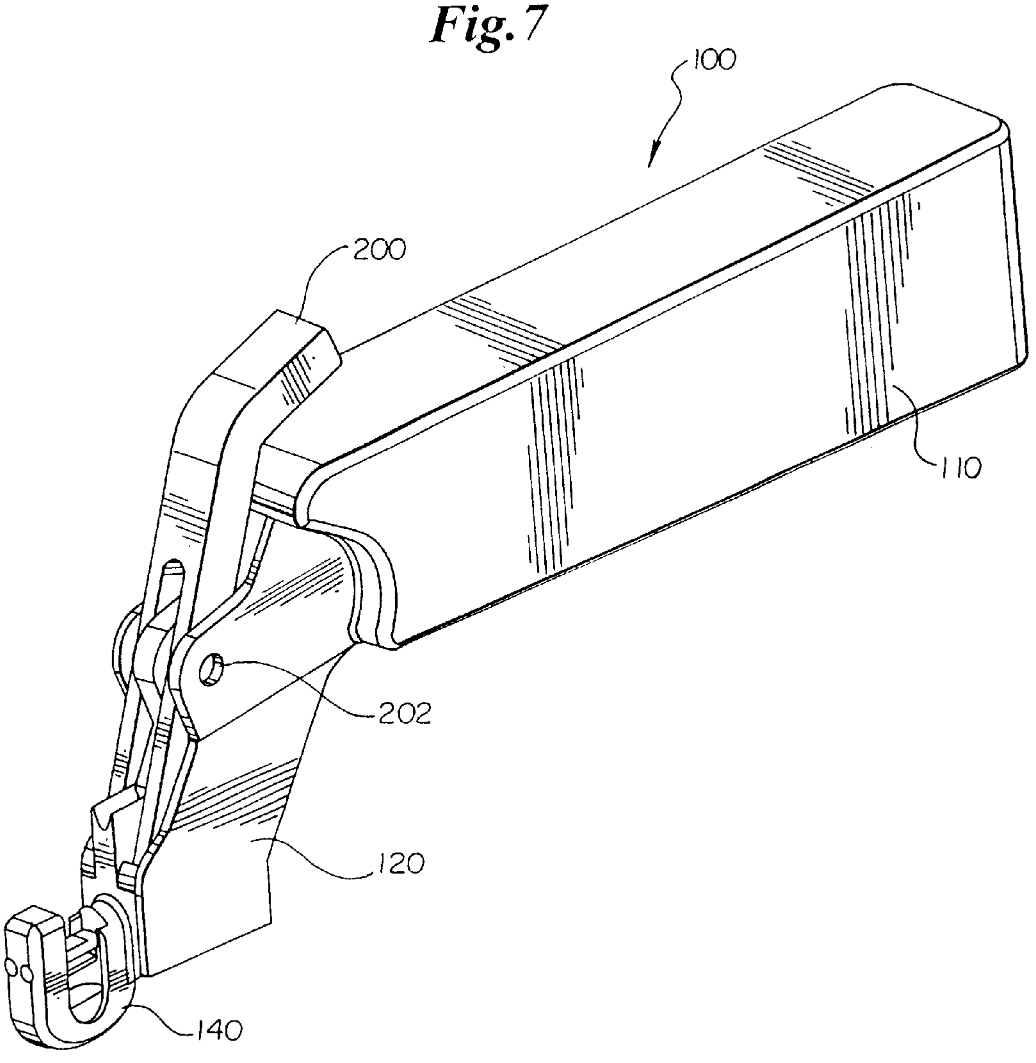
FIG. 7 is a perspective view of a currently most preferred embodiment of the applicator apparatus of the present invention.
Figure 8:
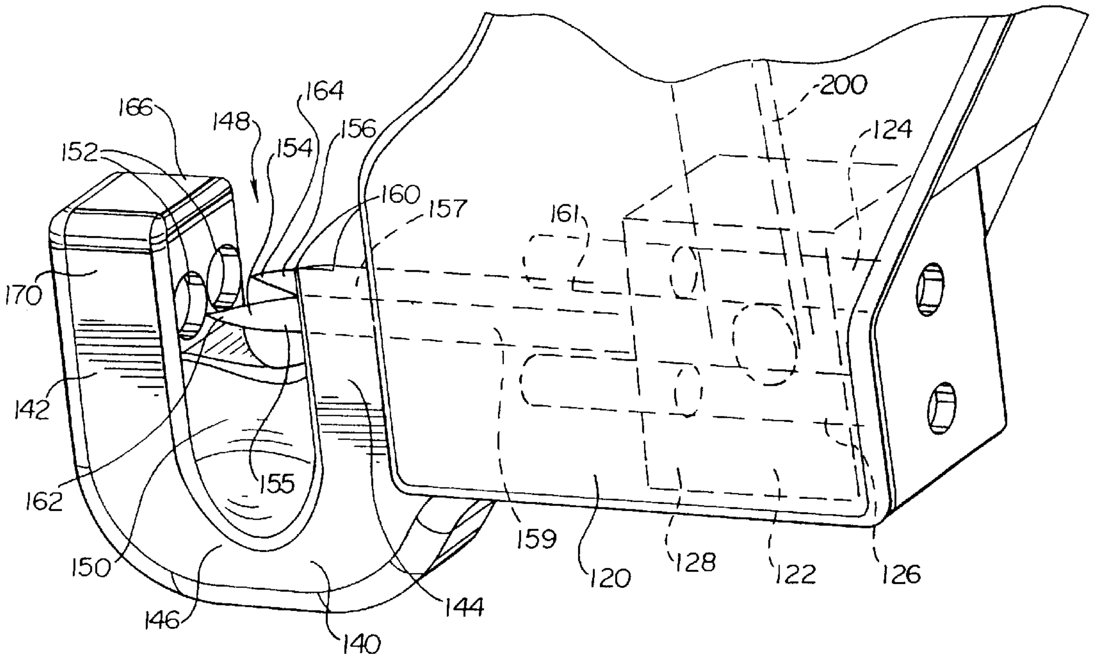
FIG. 8 is a perspective view of the lower handle and driving head portions of the applicator apparatus of FIG. 7.
Figure 9:
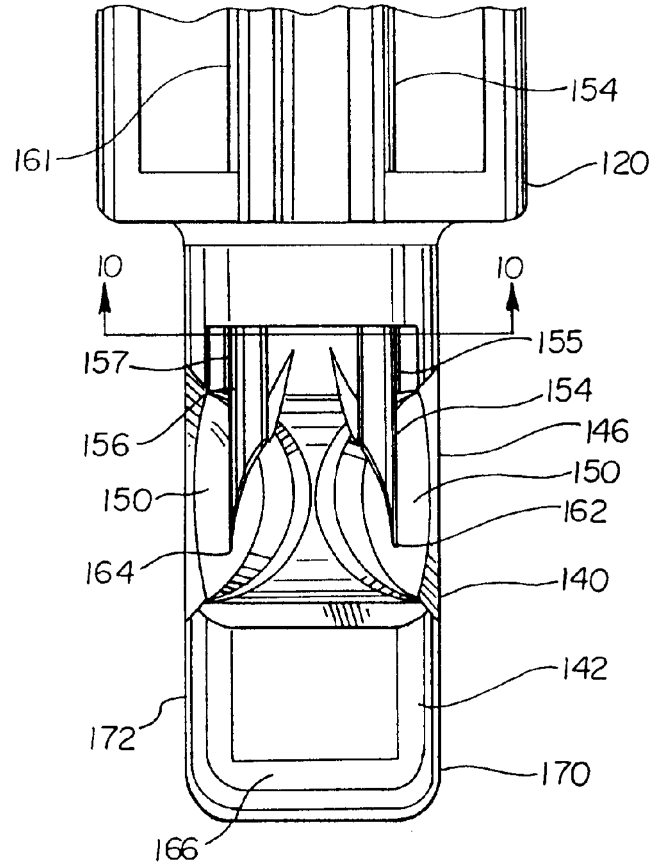
FIG. 9 is a top plan view of the lower handle and driving head portions of the applicator apparatus of FIG. 7.
Figure 10:
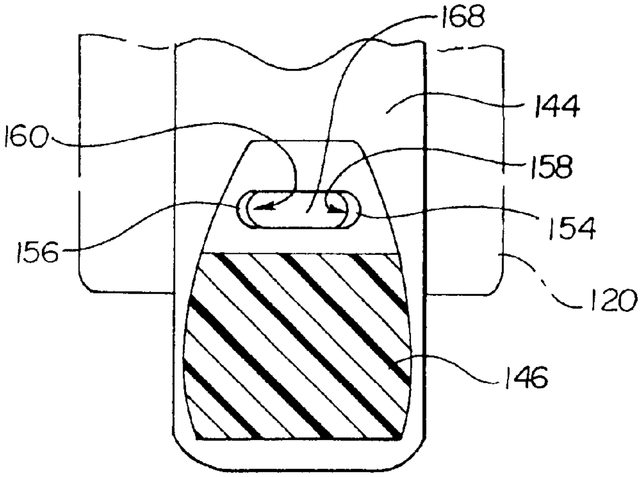
FIG. 10 is a partial cross-sectional view of the driving head portion shown in FIG. 9.
Figure 11:
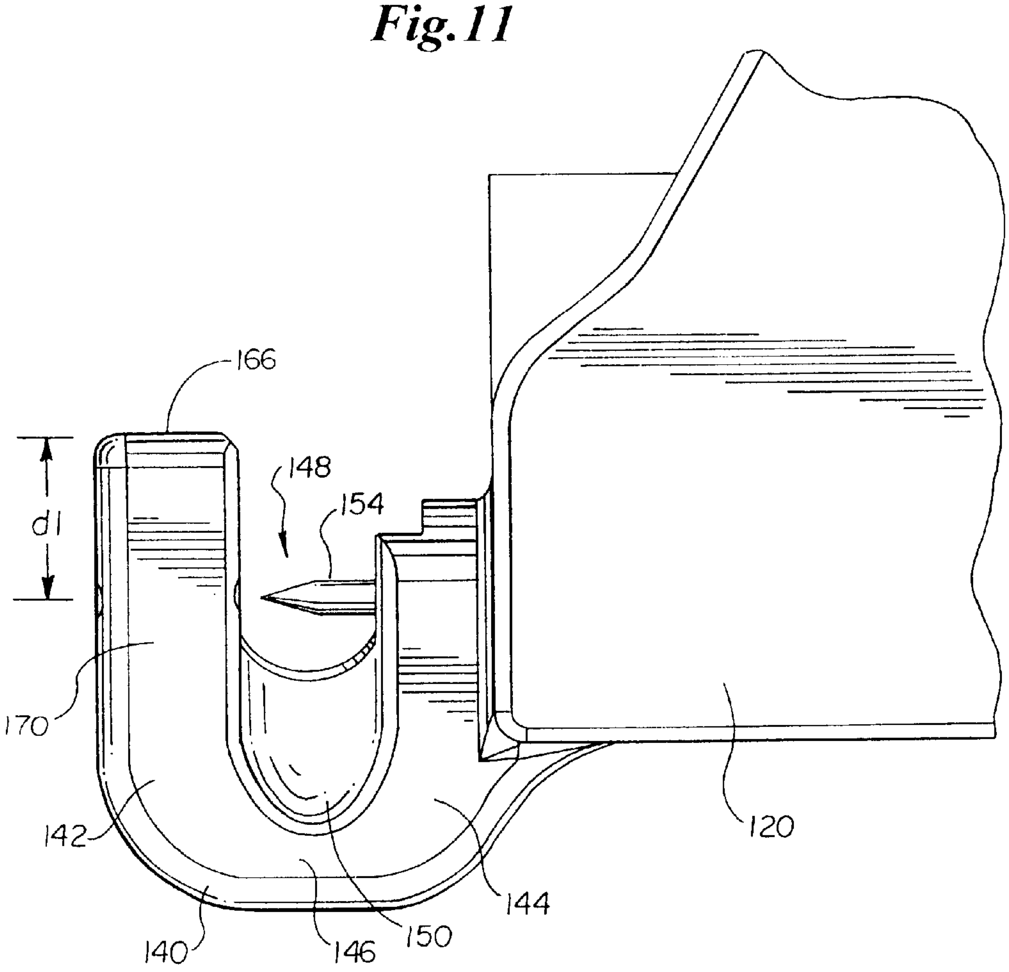
FIG. 11 is a side elevation view of the lower handle and driving head portions of the applicator apparatus of FIG. 7.

As illustrated in FIG. 6, due to the inherent flexibility and resilience of skin tissue, it is most desirable that a fastener 400 be deployed into the target tissue zone 70 while the skin opening is everted. By compressing the everted dermal layers 56 on either side of the opening 50 into the fastener 400, the dermal layers 56 are retained in close contact with each other by the fastener 400 after the everting pressure is removed and the skin relaxes into a flat condition as shown in FIG. 4.

A preferred embodiment of the apparatus of the present invention is shown in FIGS. 7–20. Generally, the apparatus includes an applicator assembly 100, a tissue manipulator assembly 300, and a fastener 400.

A preferred embodiment of applicator assembly 100 is shown in FIGS. 7–16. The assembly generally comprises upper handle portion 110 and lower handle portion 120, to which is attached driving head 140. Trigger 200, which pivots about pivot 202 is provided to allow user actuation of the mechanism. Although a manual pivoting trigger arrangement 200 is shown, it will be understood that a variety of other user-actuated manual triggers, buttons or actuator mechanisms may be utilized with the applicator assembly 100, such as a push button, slide mechanism, cam mechanism, spring actuated apparatus, cable actuated pull mechanism, rotating mechanism or tab actuated trigger. Alternatively, an automatic actuator in the form of an electronic, pneumatic, motion controlled, remote controlled or computer-activated trigger may be used to operate the applicator 100.

In FIGS. 8–13, there are shown detailed views of a preferred embodiment of a driving head 140 and lower handle portion 120. Driving head 140 is preferably U-shaped and has an anvil portion 142 separated from backing portion 144 by a cross-member 146, thereby forming a gap 148. Cross-member 146 preferably has concave areas 150, which are shaped to correspond to tissue manipulator surfaces 318 of tissue manipulator assembly 300, allowing the dermal layer 56 of skin to be compressed into contact within gap 148, and with target tissue zones 70 present for capture on either side of vertical interface 51 as will be further explained hereinbelow. Although driving head 140 is shown in a fixed orientation relative to lower handle portion 120 and upper handle portion 110, it will be understood that driving head 140 may be articulated, either in the plane of the vertical interface 51 or perpendicular to the plane of the vertical interface 51, to allow for increased maneuverability and orientation of driving head 140. Alternatively, lower handle portion 120 may be articulated relative to upper handle portion 110, or both lower handle portion 120 and driving head 140 may be articulated.

Preferably, anvil portion 144 of driving head 140 has apertures 152 formed therethrough. Apertures 152 are appropriately sized so as to slidingly receive penetrators or pilot needles 154, 156 and may be bore directly into the material of anvil portion 144 or may be lined with a metal guide tube or the like inserted into a bore in anvil portion 144. Pilot needles 154, 156 have a generally arcuate shaped cross-section throughout distal portions 155, 157, and a solid cylindrical cross-section in proximal portions 159, 161. Each distal portion 155, 157 has an inner concave surface 158, 160 for accommodating and retaining a fastener 400, and each proximal portion 159, 161 engages the back surface of the fastener 400, allowing the fastener to be advanced distally with the needles. The distal ends 162, 164 of pilot needles 154, 156 have a sharp point for penetrating skin. Pilot needles 154, 156 are vertically disposed at a distance d1 below top surface 166 of anvil portion 142. It is preferably that top surface 166 be usable as a reference datum for visually gauging whether pilot needles 154, 156 are located within target tissue zone 70. Accordingly, it is preferable that distance d1 be between 0.1 mm and 2.0 mm, and most preferably between 0.2 mm and 0.8 mm, so that when top surface 166 is aligned with the outer skin surface, pilot needles 154, 156 are located within target tissue zone 70 and most preferably within most preferred area 72.

Delivery mechanism 128 serves to eject a fastener from driving head 140. In a preferred embodiment, slide block 122 is slidably mounted on guides 124, 126, within lower handle portion 120. Slide block 122 is engaged with trigger 200 so that actuation of the trigger causes sliding movement of slide block 122. Pilot needles 154, 156 are fixedly attached to slide block 122, and extend outwardly through backing portion 144 of driving head 140 through slot 168. Thus, back and forth sliding motion of slide block 122 causes pilot needles 154, 156 to be extended and retracted from slot 168, gap 148 and apertures 152. It will be understood that any number of mechanical driving arrangements can be used to impart the necessary force to pilot needles 154, 156, or alternatively to the fastener 400 directly. Examples include sliding mechanisms, cam mechanisms, spring-operated mechanisms, screw drives, pneumatic drives, automated motion control drives, or the like.

Pilot needles 154, 156 are preferably spaced apart by an interneedle distance of between about 2.0 mm and 20 mm and most preferably between about 4.0 mm and 16.0 mm, so that when the driving head in placed within a skin opening to be fastened, and with the skin opening aligned with the approximate midpoint between the pilot needles, the pilot needles will be located within the width orientation of the target tissue zone 70.

Figure 14:
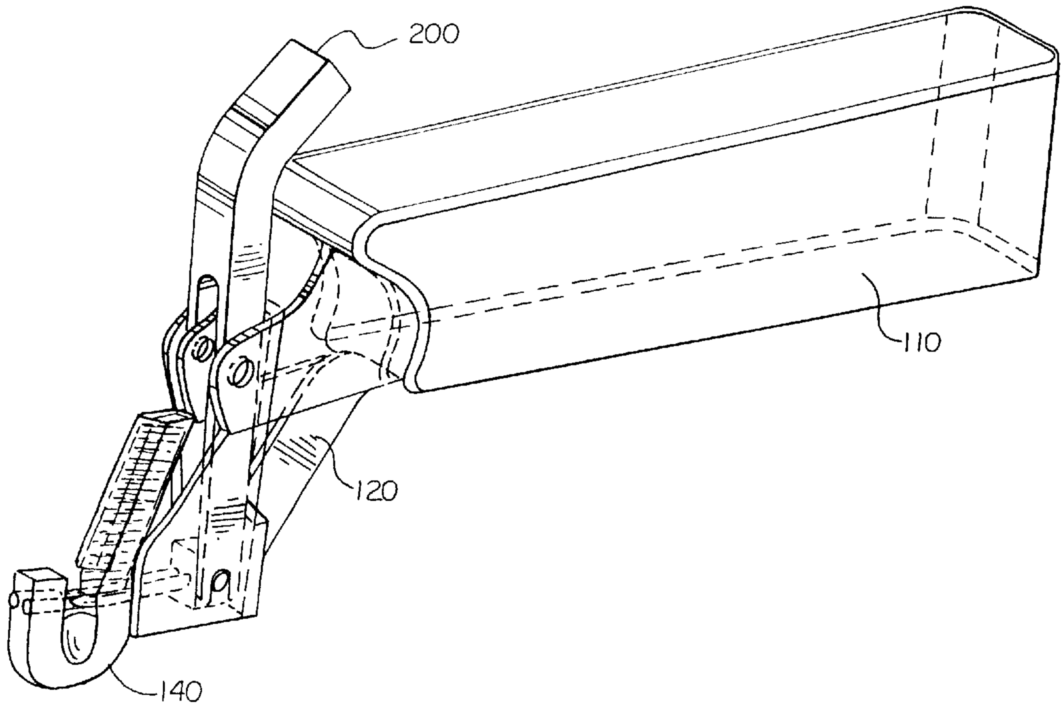
FIG. 14 is a phantom view of the applicator apparatus of a currently most preferred embodiment of the present invention having an automated fastener delivery and storage mechanism.
Figure 15:
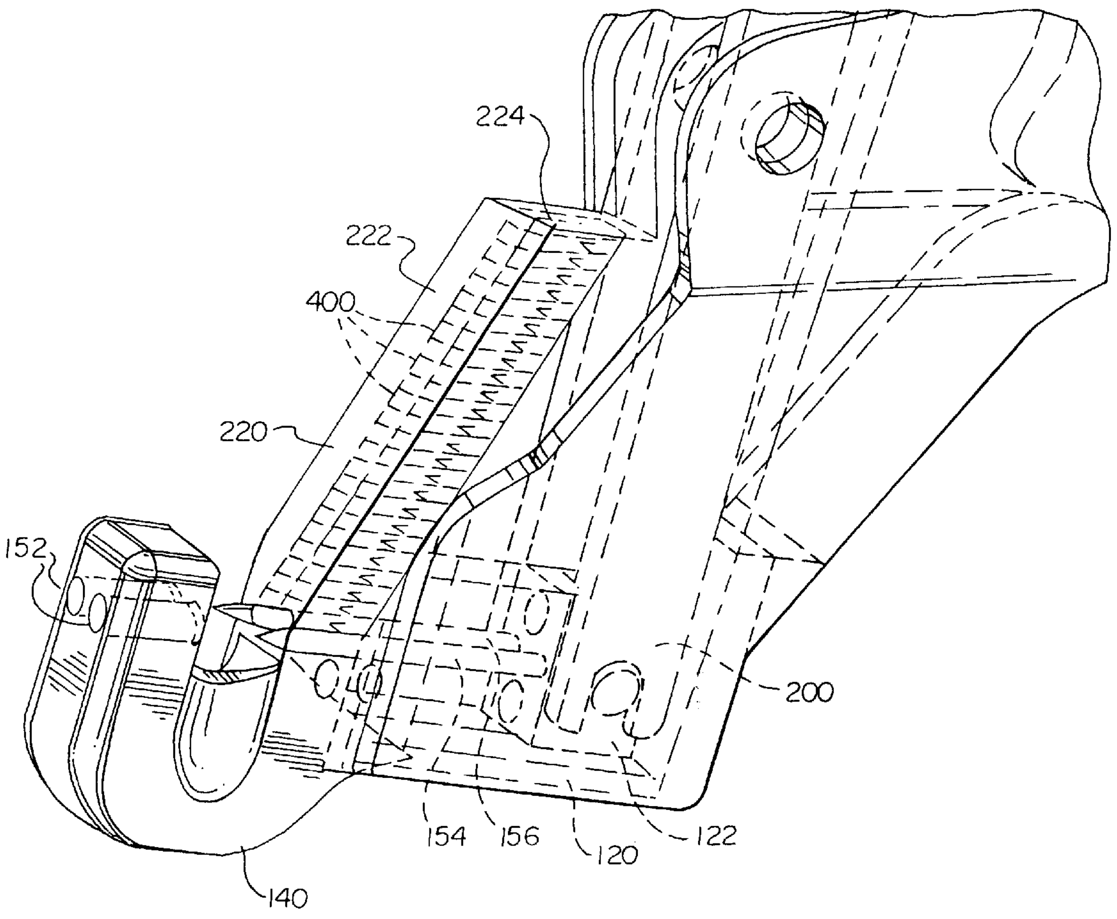
FIG. 15 is an enlarged phantom view of the apparatus of FIG. 14.
Figure 16:
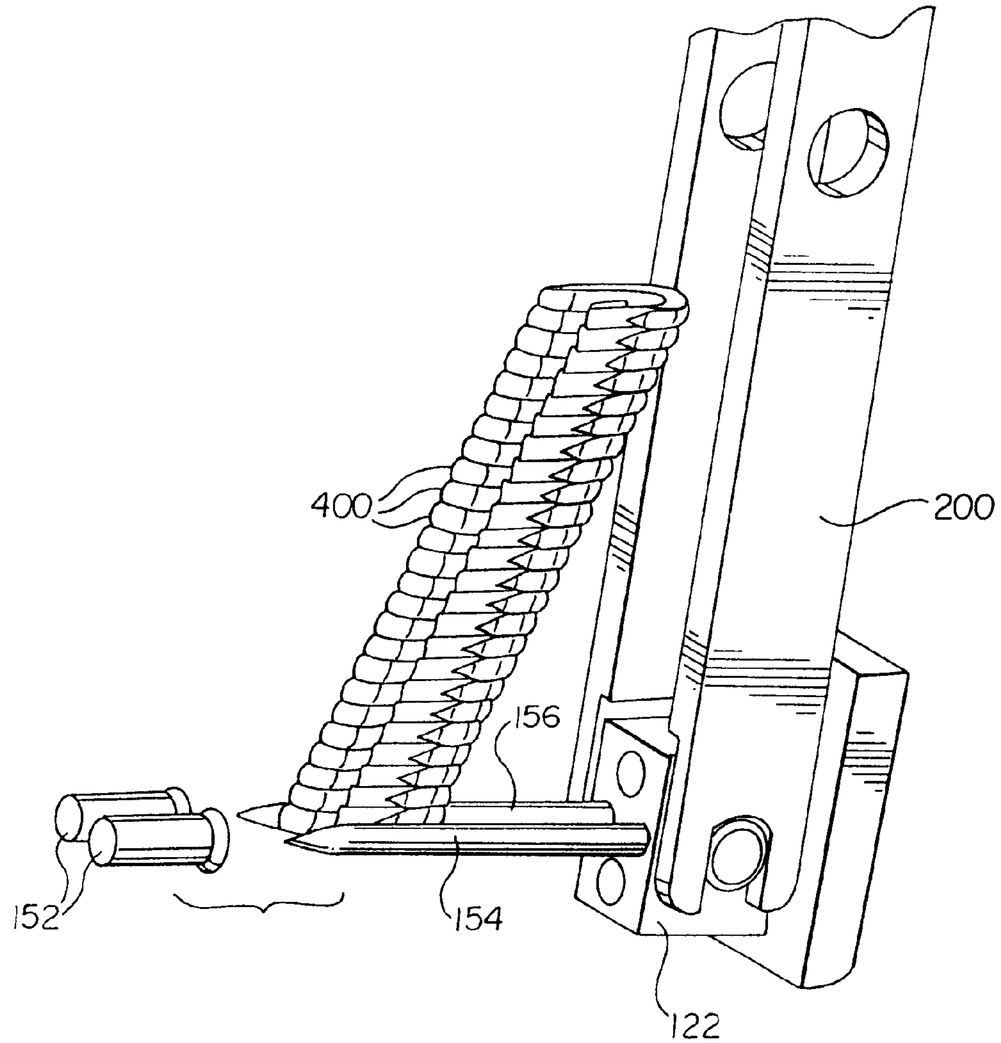
FIG. 16 is a partial view of the apparatus of FIG. 14.

Although single fasteners may be inserted manually one-by-one between pilot needles 154, 156, an alternative embodiment of applicator assembly 100, shown in phantom in FIGS. 14–16 has an automated fastener delivery and storage mechanism 220. In this mechanism, fasteners are preferably stacked vertically in echelon fashion surrounding a guide member 224, and are biased downwardly with a resilient member such as a spring (not shown). Housing 222 is provided to protect the mechanism. The bottom-most fastener in the echelon is engaged with pilot needles 154, 156. As each fastener 400 is emplaced in the skin through operation of the applicator assembly 100 as described herein, and slide block 122 is returned to the proximal limit of travel, the downward bias of the echelon causes the immediately vertical adjacent fastener to move downward and become engaged within pilot needles 154, 156. The next fastener may then be emplaced in the skin, and the process repeated. Again, it will be appreciated that numerous arrangements and configurations for providing and deploying multiple fasteners within the context of the present invention could be used, such as inline stacking in either a horizontal or vertical orientation, side-by-side stacking, rotational presentation via a circular chamber or magazine or belt or tape-attached presentation of the fasteners 400.

Figure 17:
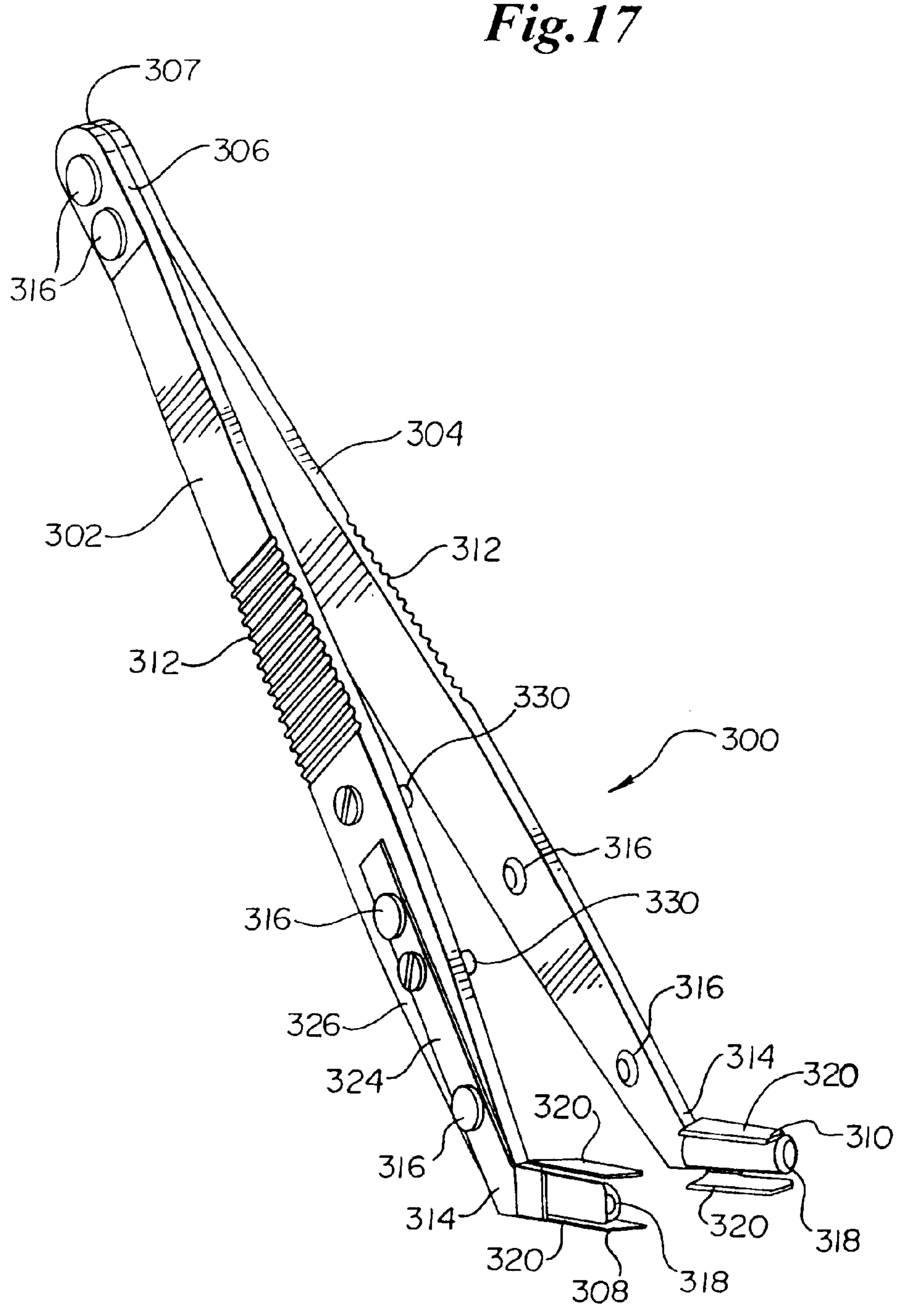
FIG. 17 is a perspective view of a currently most preferred embodiment of a manipulator apparatus according to the present invention.
Figure 18:
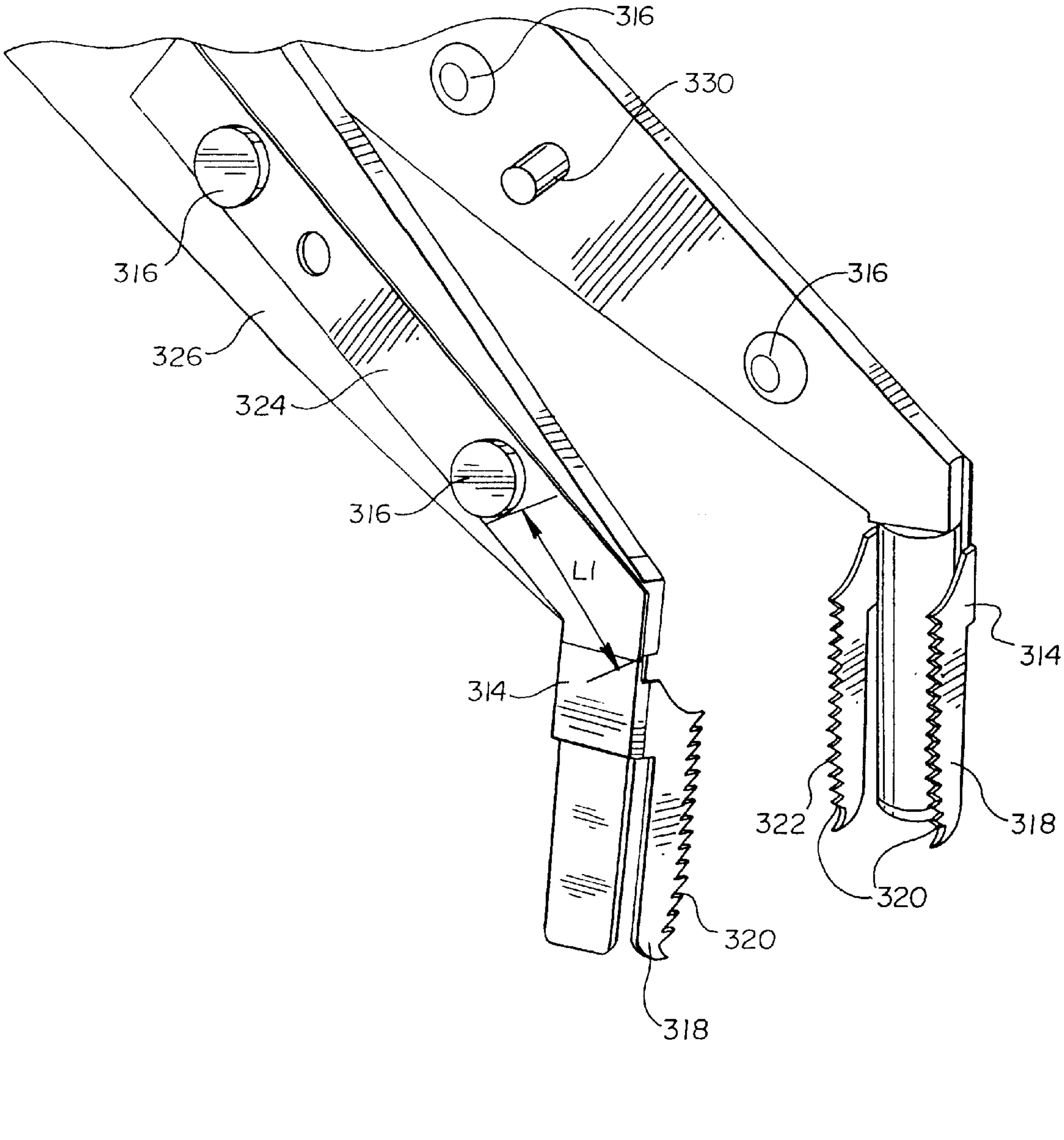
FIG. 18 is an enlarged view of the jaw portions of the manipulator apparatus of FIG. 17.

In FIGS. 17 and 18, there is shown a preferred embodiment of the tissue manipulator assembly 300 of the present invention. The proximal ends 307 of arms 302, 304 are joined together at fulcrum 306, forming the tweezer-like structure of the overall assembly. Gripping areas 312 are provided on each arm to allow gripping of the assembly with the fingers. Any suitable fastening method may be used at fulcrum 306, including rivets 316 as shown, or the arms 302, 304 may be welded, cast, or molded together or may otherwise be integrally formed together. The material and overall dimensions for arms 302, 304 are selected so as to allow the arms to be resiliently compressed inwardly with the fingers, and with a memory characteristic for returning to the original position upon the removal of pressure. In addition, the material used for the arms and other portions of the assembly are preferably thermally and chemically stable so as to allow sterilization with either heat or chemical means. The preferred material for arms 302, 304 is stainless steel.

At the distal ends 309 of each arm 302, 304 are formed tissue manipulator surfaces 318. Manipulator surfaces 318 are preferably semi-cylindrically shaped as shown, with the diametrical dimension of each semi-cylinder selected so as to conform to the diameter and shape of the concave areas 150 of applicator assembly 100. Skin gripping jaw members 314 are preferably attached to the exterior surfaces 326 of each arm member 302, 304. Each jaw member 314 has a backing portion 324 for attaching to the arms, and a pair of inwardly directed projections 320 disposed on both sides of manipulator surfaces 318. Directly opposed serrations 322 are preferably provided on the inward-most edge of each projection 320 for better skin purchase. Backing member 324 may be attached to each arm 302, 304 using any suitable attachment method, including mechanical fasteners such as the rivets 316 as shown. For reasons that will be further explained, it is preferable that each jaw member 314 is of sufficient resilience and is attached so that inwardly directed projections 320 may deflect separately from skin manipulator surfaces 318 under moderate finger pressure applied to arms 302, 304. This may be achieved through concerted selection of the material used for jaw member 314, the thickness dimension of backing member 324, and the free length L1 of each backing member 324 between the inwardly directed projections 320 and the fastener 316 closest to the distal end 309 of the arm. The objective of the design of the backing member 324 is to have the jaw members 314 engage tissue with a first force and have the manipulator surfaces 318 engage tissue between the jaw members 314 with a second force that is greater than the first force. In addition, the use of a pair of directed projections 320 on each side of the vertical interface 51 serves to stabilize the tissue laterally between the pair of projections 320.

Mechanical stops 330 are provided to prevent pressure beyond that necessary to ensure optimal approximation of tissue into gap 148 and concave portions 150 of applicator assembly 100 from being transmitted through manipulator surfaces 318. Preferably, mechanical stops 330 are set so that manipulator surfaces 318 close to a distance that is spaced apart from the inter-needle distance of pilot needles 154, 156 by a range of 0.2–0.8 millimeters, such that the total distance between mechanical stops 330 is 0.4–1.6 millimeters greater than the inter-needle distance between pilot needles 154, 156. In a preferred embodiment in which the interneedle distance is set at 3.25 millimeter, the mechanical stops 330 would allow the surfaces 318 to close to within a range of 3.65–4.85 millimeters when approximating tissue into gap 148. Although jaw members 314 may be formed from any suitable material, the preferable material is stainless steel.

Figure 19:
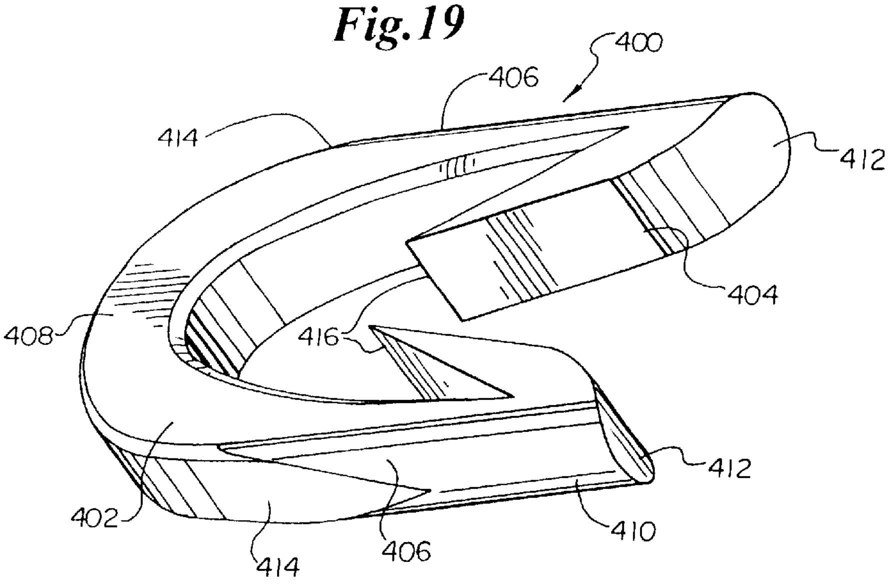
FIG. 19 is a perspective view of a currently most preferred embodiment of a fastener according to the present invention.
Figure 20:
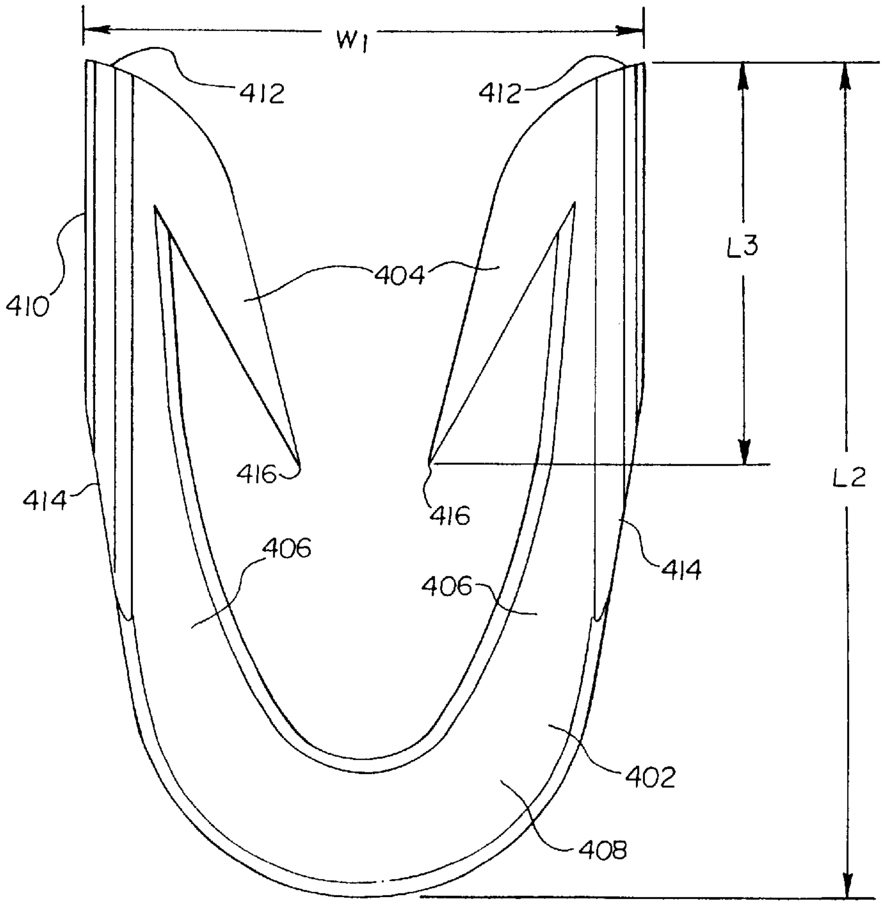
FIG. 20 is a top plan view of the fastener depicted in FIG. 19.

In FIGS. 19 and 20 there is shown a preferred embodiment of a fastener 400 of the present invention. Fastener 400 has body portion 402, which comprises a cross-member 408 connecting a pair of fork members or legs 406. The outer margins 410 of each leg 406 are dimensioned and shaped accommodatingly to the inner concave surfaces 158, 160, of pilot needles 154, 156, allowing fastener 400 to fit and slide between the distal portions 155, 157 of the needles, as is shown best in FIGS. 12 and 13. Shoulders 414 preferably are provided to engage the solid cylindrical cross-section of the proximal portions 159, 161 of pilot needles 154, 156, thus allowing fastener 400 to be advanced distally with motion of the needles. The distal end 412 of each leg 406 is incurvately shaped to allow easier passage through an opening in skin, referred to as a skive, that is created by pilot needles 154, 156. Inwardly directed barbs 404 preferably are provided on each leg 406 to resist withdrawal of the fastener once emplaced.

Although an overall U-shape for the fastener 400, as shown in FIGS. 19 and 20 is preferred, other shapes having a capability for bilateral tissue engagement are also possible and within the scope of the invention. Such other shapes include for example, but are not limited to, a square shape similar to an ordinary staple, a semi-circular or C-shape or a V-shape or W-shape in which the cross-member 408 has bends or other features. While the shape of fastener 400 is generally determined in a planar configuration, it will be recognized that other non-planar shapes and configuration can be used, such as a fastener having multiple projections for each leg 406, with each projection oriented in a different plane, or a fastener having cross-member 408 arranged in a V-shape projecting out of the normal plane of the fastener 400. Two leg members 406 are preferred, but it will be understood that additional leg members 406 could be added in the same or a different plane of the fastener 400 such that the leg members of each side of the fastener form a dident or trident configuration, for example.

Figure 39:
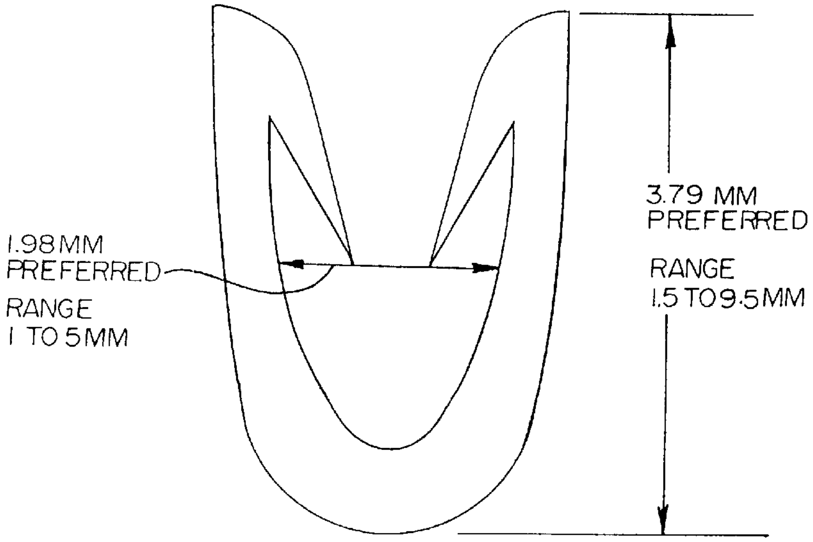
FIG. 39 is a plan view of a preferred embodiment of a fastener showing the inner cross-sectional area.

As shown in FIG. 39, an inner cross-sectional area 409 is defined by the fastener 400 for capturing the compressed dermal tissue. In a preferred embodiment, inner cross-sectional area 409 ranges from 1.5 sq. mm to 50 sq. mm and most preferably about 5 sq. mm to 10 sq. mm. This area is generally defined by an inner diameter length of between 1.5 mm and 9 mm and most preferably about 3.8 mm and an inner diameter width of between 1 mm and 5 mm and most preferably about 2 mm. It will be apparent that numerous shapes and configurations can be used for the shape and arrangement of cross-sectional area 409. Preferably, inner cross-sectional area 409 is generally arrowhead shaped as a result of the positioning of the barbs 412. As will be described, the barbs 412 or similar anti-reversing projections resist against the withdrawal of fastener 400. While the barbs 412 are preferably oriented into the inner cross-sectional area 409, it will be appreciated that barbs 412 may be omitted or may be oriented outwardly.

Although it is possible for fastener 400 to be deformed during delivery and application, preferably the majority of dermal tissue retained within cross-sectional area 409 is captured in a compressed state by a fastener 400 that is sufficiently rigid so as to retain the dimensional integrity of cross-sectional area 409 within +/−30% of its designed area for a period of preferably at least 10 days. Most preferably, structural integrity of fastener 400 is maintained for at least 21 days. In this way, the dermal tissue captured in fastener 400 is retained in a compressed state for a period sufficient to allow the biological healing process to occur without the dermal tissue being under tension during the healing process. Preferably, the dimensions of the fastener 400 and the operation of the applicator assembly 100 coordinate to create a compression ratio of dermal tissue within the inner cross-sectional area 409 that is greater than one. The compression ratio is defined either as a ratio of area or a ratio of width. In the case of width, the compression ratio is the ratio of the dimension defined by the position of the skive relative to the vertical interface 51 when the dermal tissue is at rest divided by the position of the skive relative to the vertical interface as held by the fastener 400. In the case of area, the compression ratio is the ratio of the area of dermal tissue that will be retained by the fastener 400 when that dermal tissue is at rest divided by the actual cross-sectional area 409.

Alternatively, it is possible to take advantage of the bilateral tissue fastening in the tissue target zone as taught by the present invention with a deformable fastener where the deforming of a bioresorbable or bioabsorbable fastener serves to provide at least some of the compression of the dermal tissue such that the need for a mechanical tissue manipulator is reduced or potentially eliminated. In this embodiment, a bioresorbable or bioabsorbable fastener would be deformed by the applicator apparatus in order to appropriately compress the dermal tissue. Deformation of a bioresorbable or bioabsorbable fastener could be accomplished in a number of ways, including prestressing the fastener into an open configuration such that it returns to a closed configuration, with or without mechanical assistance from the applicator, application of ultrasound, heat or light energy to alter the shape of, or reduce or relax stresses in, the fastener in situ, designing a polymer material with appropriate shapes and compositions that the material is deformable upon deployment without fracturing, or any combination of these techniques.

Fastener 400 is preferably formed from any suitable biodegradable material. The currently most preferred biodegradable material is a lactide/glycolide copolymer where the ratio is never less than at least 10% of one element and preferably in a range of 60%–70% lactide. Examples of other suitable materials include poly(dl-lactide), poly(l-lactide), polyglycolide, poly(dioxanone), poly(glycolide-co-trimethylene carbonate), poly(l-lactide-co-glycolide), poly (dl-lactide-co-glycolide), poly(l-lactide-co-dl-lactide) and poly(glycolide-co-trimethylene carbonate-co-dioxanone). In addition, other suitable materials could include compositions with naturally occurring biopolymers such as collagen and elastin, or stainless steel, metal, nylon or any other biocompatible materials in the case of a non-absorbable fastener, or even various combinations of such materials depending upon the desired application and performance of the fastener.

Figure 12:
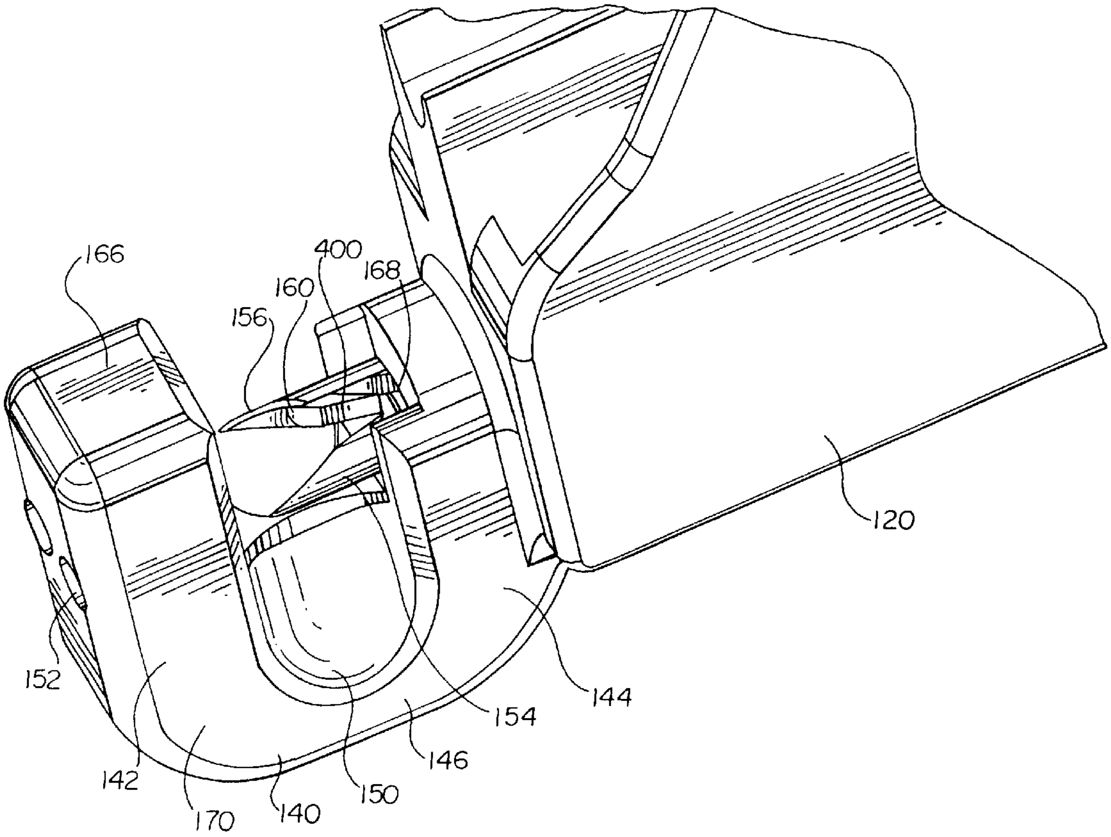
FIG. 12 is a perspective view of the lower handle and driving head portions as depicted in FIG. 8 with a fastener positioned therein.
Figure 13:
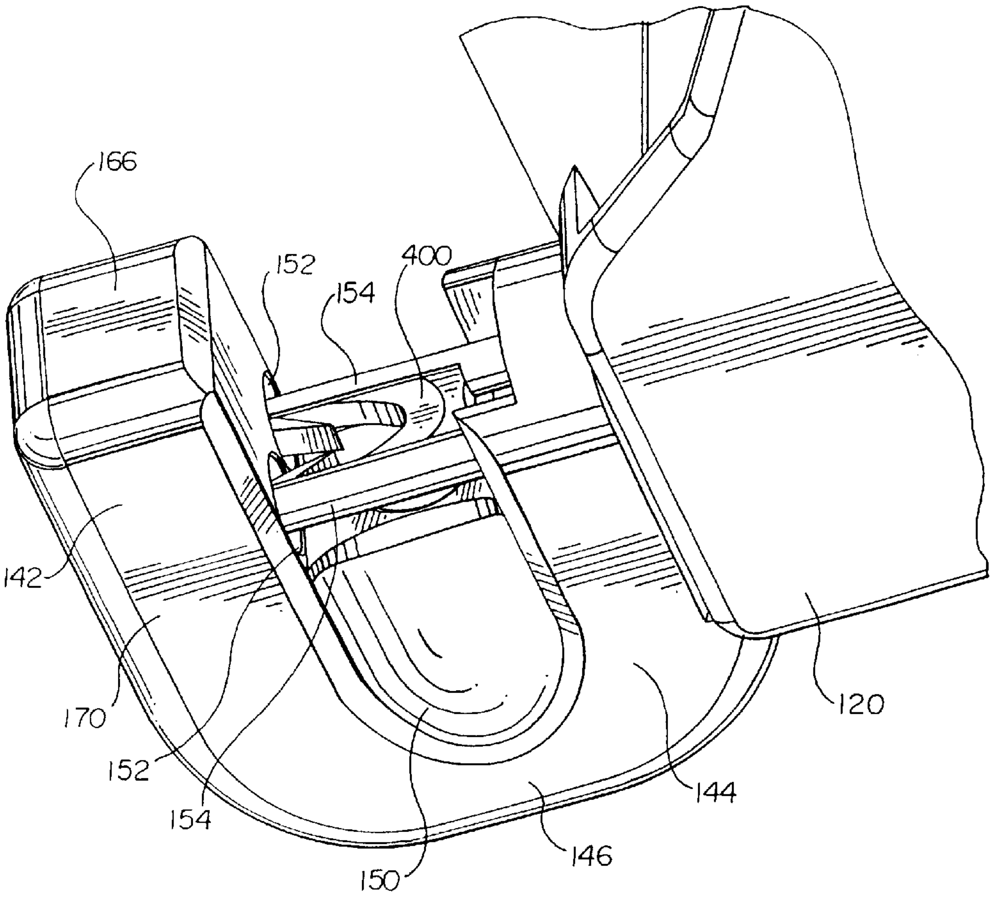
FIG. 13 is another perspective view of the lower handle and driving head portions as depicted in FIG. 8 with a fastener positioned therein.
Figure 21:
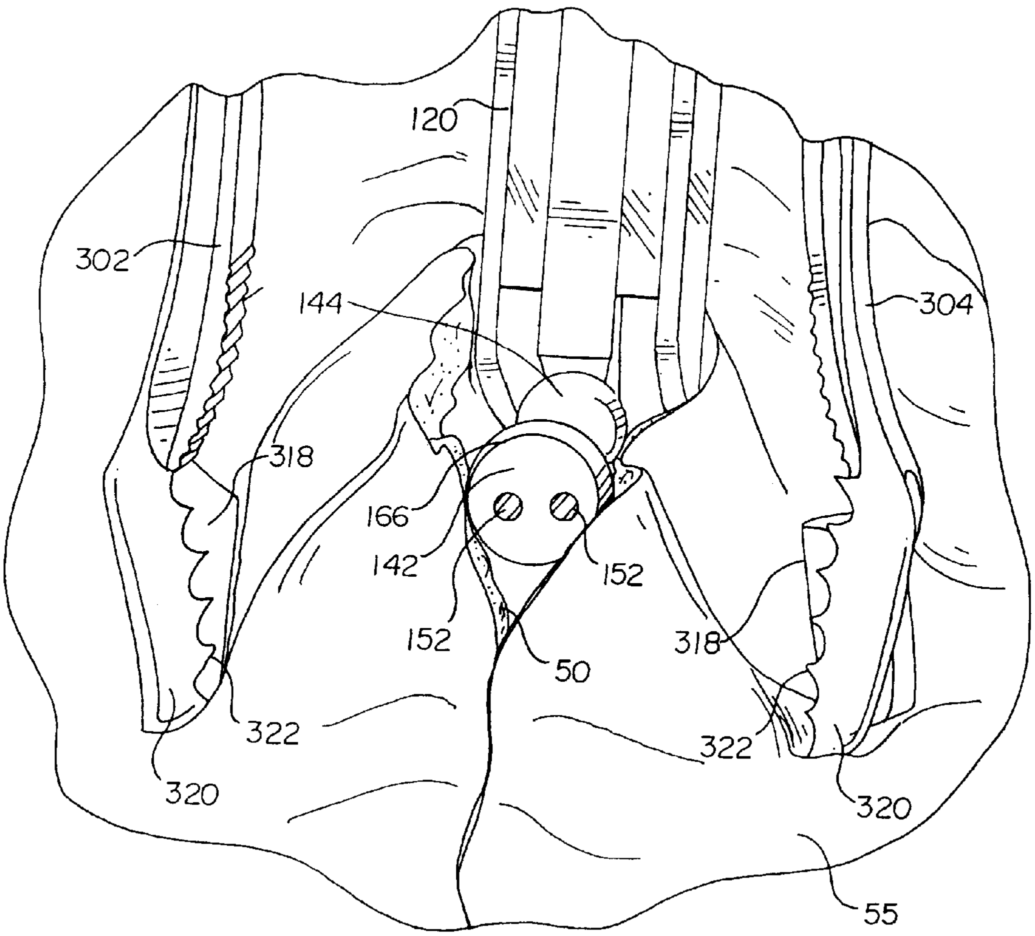
FIG. 21 is a perspective view showing the orientation of applicator and manipulator apparatus during a step of a currently most preferred embodiment of the method of the present invention.
Figure 22:
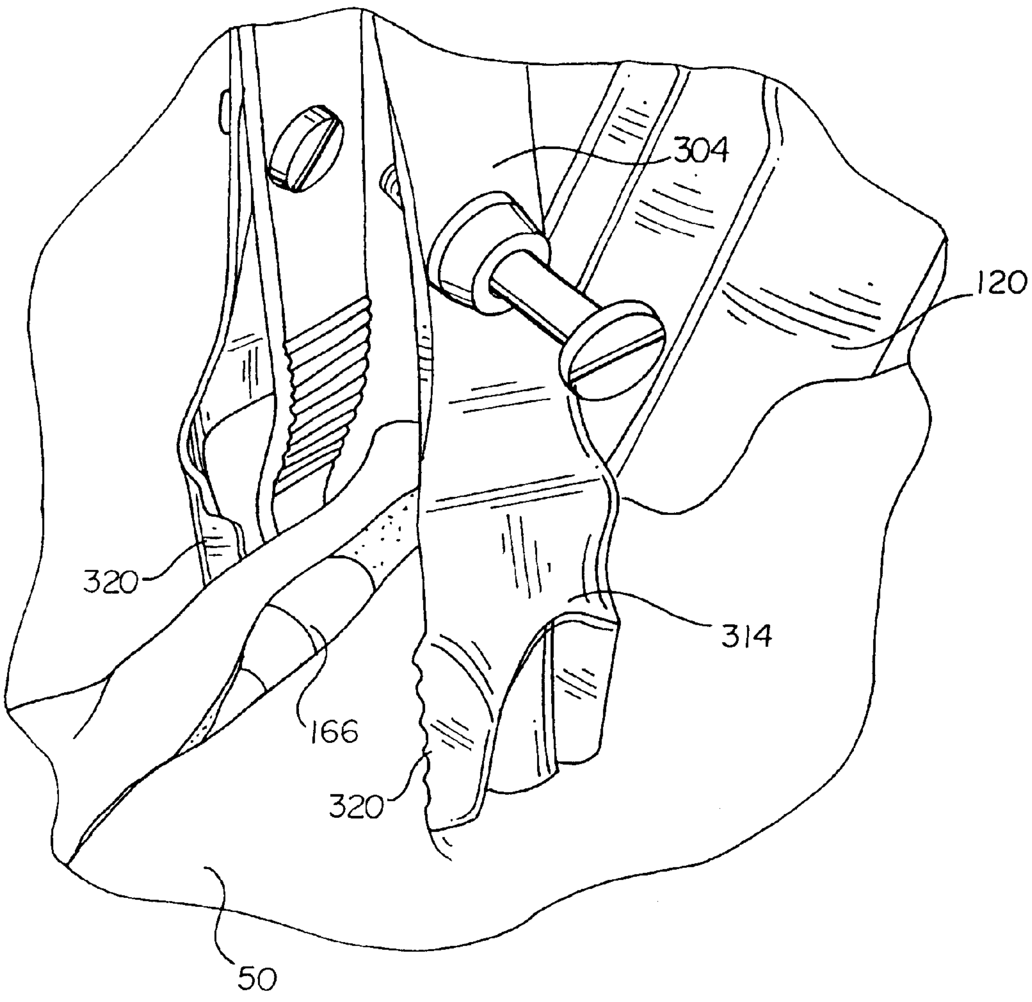
FIG. 22 is a perspective view of the apparatus during another step of the method of the present invention.
Figure 23:
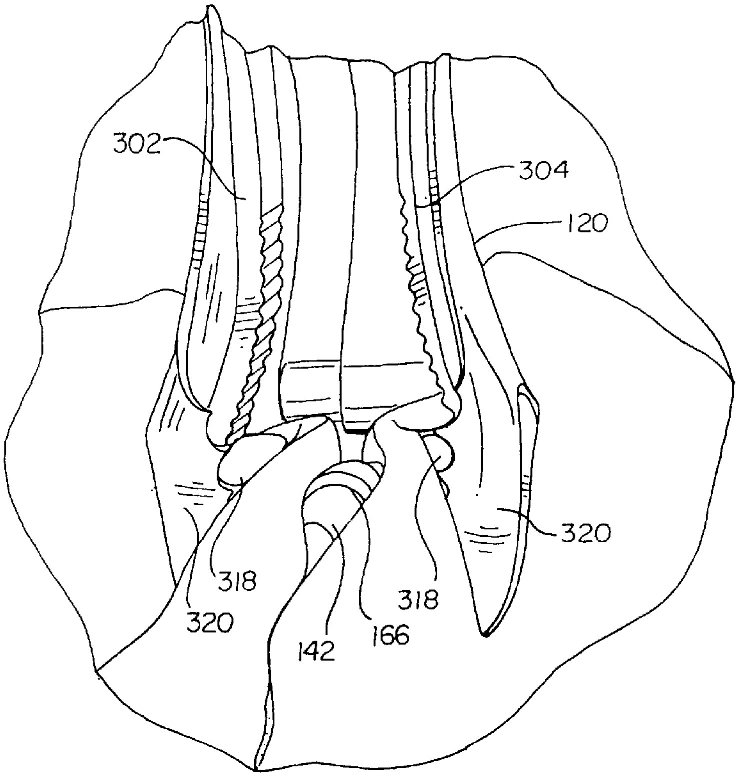
FIG. 23 is a perspective view of the apparatus during yet another step of the method of the present invention.
Figure 24:
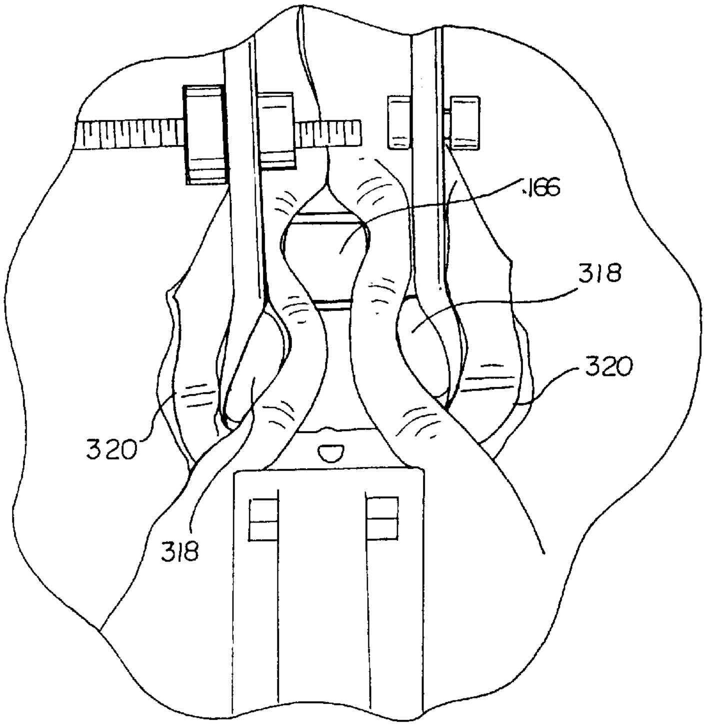
FIG. 24 is a perspective view of the apparatus during still another step of the method of the present invention.
Figure 25:
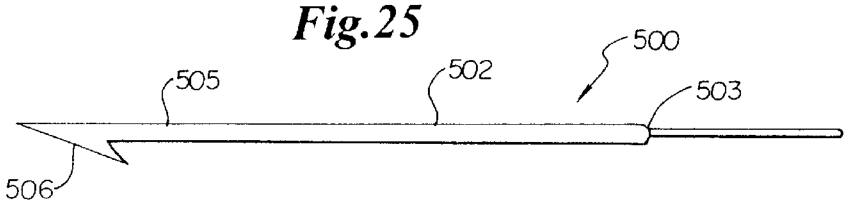
FIG. 25 is a top plan view of an alternative embodiment of a fastener according to the present invention.
Figure 26:
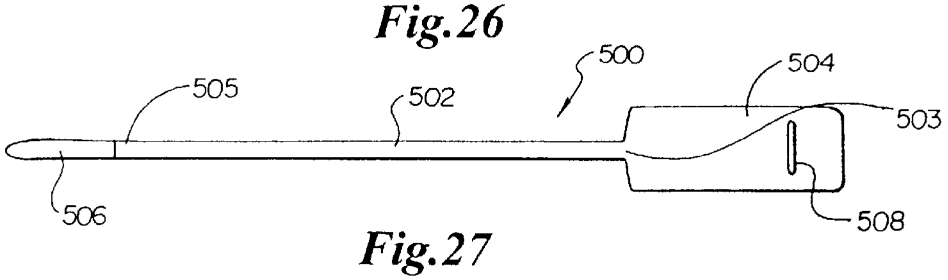
FIG. 26 is a side elevation view of the fastener of FIG. 25.
Figure 27:
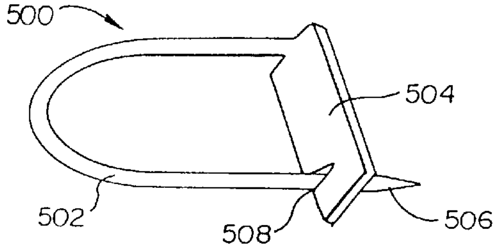
FIG. 27 is a view of the fastener of FIG. 25 in a deployed condition.
Figure 28:
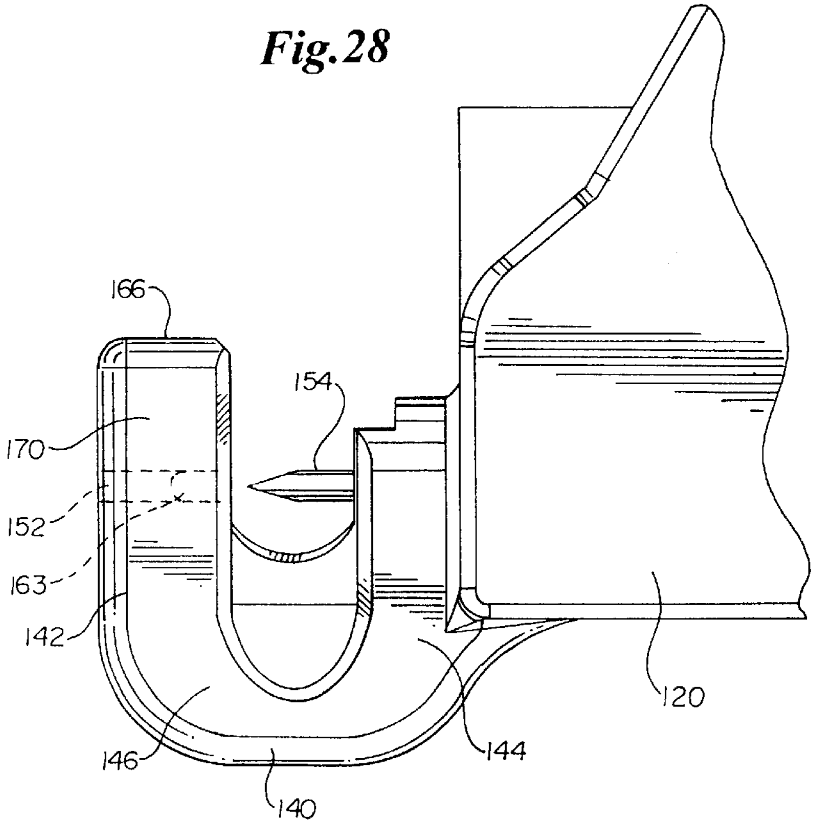
FIG. 28 is a view of an applicator assembly according to an alternative embodiment of the invention.
Figure 29:
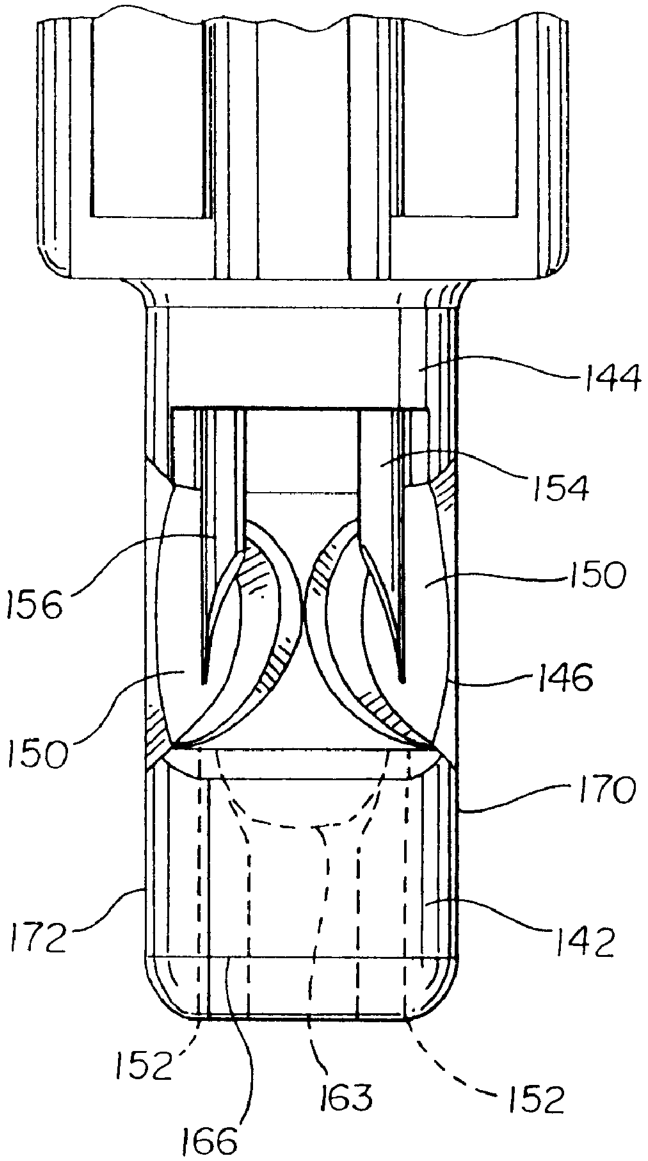
FIG. 29 is another view of an applicator assembly according to an alternative embodiment of the invention.

With reference to FIGS. 21–24, the operation of the apparatus of the present invention may now be explained and understood. A fastener 400 is first loaded between pilot needles 154, 156, as shown in FIG. 12. Slide block 122 is then proximally retracted to the fullest extent so that pilot needles 154, 156 and the fastener 400 are entirely within slot 168. Driving head 140 is then introduced into skin opening 50 and top surface 282 is aligned with the outer surface of the skin as shown in FIG. 21. Tissue manipulator assembly 300 is placed with jaw members 314 on either side of driving head 140. Arms 302, 304 of manipulator assembly 300 are pressed inward so that jaws 314 engage the skin surface and begin to force the skin 52 into gap 148 in applicator assembly 100 as shown in FIG. 22. Serrations 322 provide purchase on the skin surface and prevent lateral slipping of the skin relative to the jaws. As further inward pressure is applied to arms 302, 304, inwardly directed projections 320 engage side surfaces 170 of anvil portion 142 and side surfaces 172 of backing portion 144, each with a single thickness of skin trapped between as shown in FIG. 23. Still further inward pressure on arms 302, 304, as shown in FIG. 24, causes tissue manipulator surfaces to deflect inward slightly from jaws 314, until each engages concave area 150 of cross-member 146 with a layer of skin trapped in between. In this position, inner surfaces 60 of dermal layer 56 are in direct contact with each other within gap 148 and substantially parallel with vertical interface 51, but are not overlapped or interdigitated.

In this preferred embodiment, pilot needles 154, 156 are aligned generally horizontally and substantially parallel with the outer surface of the skin and are within target tissue zone 70. Cross-member 408 of fastener 400 is positioned generally transverse to vertical interface 51 and a working plane of fastener 400 defined by cross-member 408 and legs 406 is generally horizontal in orientation. Trigger 280 is then actuated, causing slide block 122 to move proximally within lower handle portion 120, and advancing pilot needles 154, 156 into the skin, creating a skive through the target tissue zone 70 of the skin on each side of vertical interface 51. Fastener 400 moves with pilot needles 154, 156, and each leg 406 of the fastener 400 is simultaneously driven into and through the skive. Once fastener 400 is advanced distally a sufficient distance so that barb tips 416 of fastener 400 enter apertures 152 and accordingly emerge from the skive, trigger 280 may be reversed so that slide block 122 moves proximally, retracting pilot needles 154, 156. Barbs 412 engage the skin, thereby preventing fastener 400 from being withdrawn with the pilot needles. Once slide block 122 has been fully retracted proximally, thereby causing pilot needles 154, 156 to be fully retracted from gap 148, the pressure on manipulator assembly 300 may be released and applicator assembly 100 can be moved proximally in the opening 50 to deliver another fastener 400 or can be removed from opening 50.

In addition to the preferred embodiment of the apparatus described above wherein the legs of a fastener are simultaneously driven through the target tissue zone on each side of the skin opening and with the fastener legs oriented parallel to the epidermal skin surface, those of skill in the art will appreciate that other embodiments of a mechanical fastening system for openings in skin tissue are within the scope of the present invention. For instance, the working plane of fastener 400 defined by cross-member 408 and legs 406 may be oriented generally orthogonal, or oblique in at least one orientation, to the horizontal plane generally defined by exterior surface 55 of epidermal layer 54. In such an embodiment, fastener 400 may be inserted in a generally vertical orientation with legs 406 pointing generally in an upward direction or in a downward direction.

Another embodiment of the apparatus of the present invention wherein a fastener is driven sequentially through the bilateral target tissue zones is shown in FIGS. 25–29. In one embodiment, fastener 500 has flexible body portion 502 with a barb 506 at distal end 505 and an attachment flap 504 at proximal end 503. Flexible body portion 502 is dimensioned so as to be received within either concave inner surface 158, 160 of pilot needles 154, 156. Attachment flap 504 has slot 508 formed therethrough, which is adapted to receive barb 506. In applicator assembly 100, anvil portion 142 has concave deflector 153 formed between apertures 152 and extending into a portion of each aperture 152 so that only an area of each aperture is open sufficient to allow the arcuate cross-section of pilot needles 154, 156 to pass. In operation, and with reference to FIGS. 1–29, fastener 500 is axially aligned with pilot needle 154, and is inserted within the corresponding concave inner surface of the needle with barb 506 oriented toward the point of the needle. Applicator assembly 100 is then introduced into the interface portion 51 of the skin opening 50 as described above. Tissue manipulator assembly 300 is then applied as before to bring the dermal layer 56 into contact within gap 148, and thereby properly positioning target tissue zone 70. As slide block 122 and the attached pilot needles 154, 156 are moved distally through actuation of trigger 280, fastener 500 is advanced through the skin tissue on one side of skin opening 50 along with pilot needle 154 in which it is disposed. Once the tip of barb 506 reaches aperture 152, however, it is engaged by, and begins to slide laterally along, concave deflector 163, causing flexible body portion 502 to bend. As pilot needles 154, 156 are further advanced, barb 506 is turned in direction 180 degrees by deflector 163. It will be appreciated that the barb 506 may either be positioned in front of pilot needle 154 by an amount sufficient to redirect barb 506 into the opposite direction or pilot needle 154 may advance into the corresponding aperture 152 to a depth at which the redirection of barb 506 upon the entry to aperture 152 will be sufficient to redirect barb 506 into the opposite direction. Once redirected and positioned in line with the second skive, barb 506 is advanced in the opposite direction by pilot needle 156 and through the skin tissue on the opposite side of the vertical interface 51 as pilot needle 156 is withdrawn. Once barb 506 emerges from the dermal tissue, attachment flap 504 may be bent so that barb 506 may be pushed through slot 508, thus securing fastener 500 in a loop and bilaterally capturing both sides of the skin opening 50. It will also be appreciated that attachment flap 504 may be replaced by suitable structure on flexible body 502 for engaging a suture. The suture lock of co-pending application entitled "SUTURE LOCK HAVING NON-THROUGH BORE CAPTURE ZONE," application Ser. No. 10/166,161, filed Jun. 10, 2002 which is commonly owned by the assignee of the present invention and the disclosure of which is hereby incorporated by reference, may then be used to secure the suture to barb 506, completing the bilateral capture. In this embodiment described herein, the skives are created simultaneously and the fastener 400 is inserted sequentially into each corresponding skive from an opposite direction. Alternatively, a single U-shaped needle could be utilized in place of pilot needles 154, 156 and both the skives and fastener could be created and inserted sequentially. Numerous other combinations of bilateral creation of skives and insertion of fasteners are contemplated by scope of the present invention.

As described herein, the fastener is oriented so that a working plane defined by the flexible body 502 of fastener 500 is substantially parallel to a plane generally defined by exterior surface 55 of epidermal layer 54, and transverse to vertical interface 51. Those of skill in the art will appreciate, however, that the working plane of fastener 500 could also be oriented substantially orthogonal, or oblique, with the plane generally defined by exterior surface 55 while remaining in a transverse orientation with respect to vertical interface 51. Those of skill in the art will also appreciate that other bilateral capture mechanical fastening systems wherein the target tissue zones are penetrated by a fastener in sequential fashion are possible within the scope of the present invention. For instance, a semi-circular, oval, or spiral fastener may be advanced sequentially through target tissue zones 70 on each side of vertical interface 51 using a mechanism that imparts a rotational motion to the fastener, but without causing interdigitation or overlapping of skin across vertical interface 51. The mechanism may have means for creating a semi-circular, oval or spiral skive through which the fastener may be advanced, or the fastener itself may be formed from sufficiently rigid material and have a sharpened point so as to be capable of creating a skive as it passes through the skin. In another alternative embodiment providing a sequential bilateral capture motion, a fastener is provided having a cross-member connecting two legs wherein the legs are staggered so that when the fastener is advanced into the skin in a linear fashion, one of the legs precedes the other. In still another embodiment, two straight fasteners comprising a shaft portion with skin-engaging barbs are provided. These fasteners are oriented in opposite directions on either side of the vertical interface 51, and are sequentially advanced through respective skives by an applicator assembly allowing a reversible motion.

Figure 34:
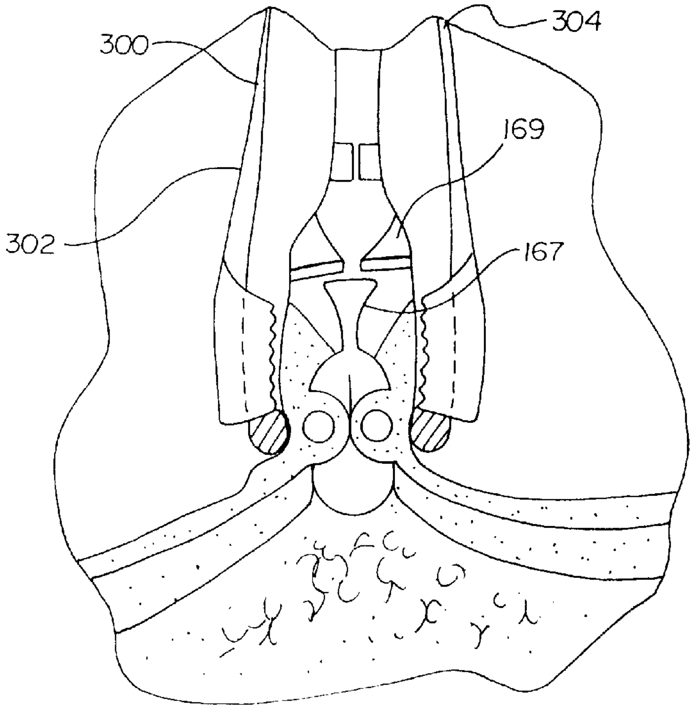
FIG. 34 is a longitudinal cross-sectional view of an alternative embodiment of the present invention showing operation of corresponding guiding features on the tissue manipulator and the applicator.

In one embodiment, as shown in FIG. 34, a tab or other similar guiding structure 167 projects from an exposed portion of anvil portion 140 to serve as a reference guide to locating the external surface of the skin against such guiding structures. Most preferably, this guiding structure 167 is adapted to mate with a corresponding pair of surface guiding features 169 on the internal surface of arms 302, 304 of the tissue manipulator assembly 300 so as to provide both a tactile and visual indication of the appropriate positioning of the applicator 100 and tissue manipulator 300 relative to the vertical interface 51 of the tissue opening 50. Preferably, the guiding structure 167 and guiding features 169 combine to force the applicator 100 to stay laterally centered about the vertical interface 51 and to stay properly positioned both horizontally and vertically. Alternatively, visual indicators and/or an exterior platform-like structure around the exterior of driving head 140 may be provided to assist the user in proper positioning of the applicator assembly 100 and the tissue manipulator assembly 300.

Figure 35:
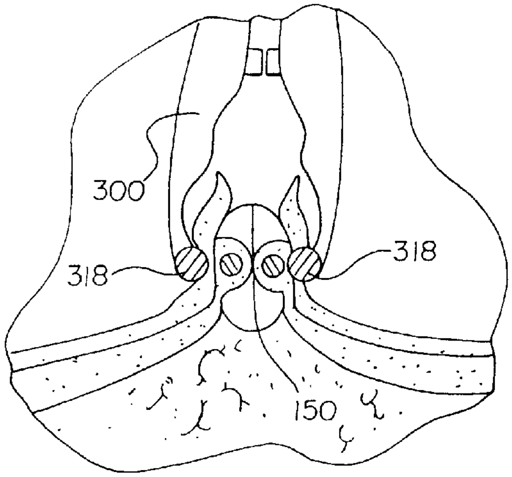
FIG. 35 is a longitudinal cross-sectional view of an alternative embodiment of the present invention showing ball tip ends on the tissue manipulator and corresponding semi-spherical areas on the applicator.
Figure 36:
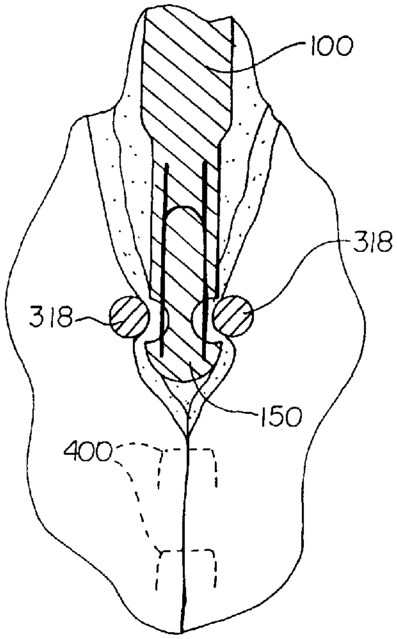
FIG. 36 is a top cross-sectional view of the alternative embodiment shown in FIG. 35.

FIGS. 35 and 36 show an alternate embodiment of applicator assembly 100 and tissue manipulator assembly 300 in which both manipulator surfaces 318 and concave areas 150 are semi-spherically shaped to provide guiding structure in both horizontal and vertical orientations as the tissue is compressed by the tissue manipulator 300 into the applicator 100. In this embodiment, there are no inward projections 320 shown for capturing the tissue as the application of pressure to the ball-like tips 318 provides both the capture and compression forces imparted to the tissue. Areas 150 on the applicator 100 are semi-spherical in shape to mate in more than one orientation with the ball tips 318, rather than being merely concave to align the tissue in a single orientation.

Figure 37:
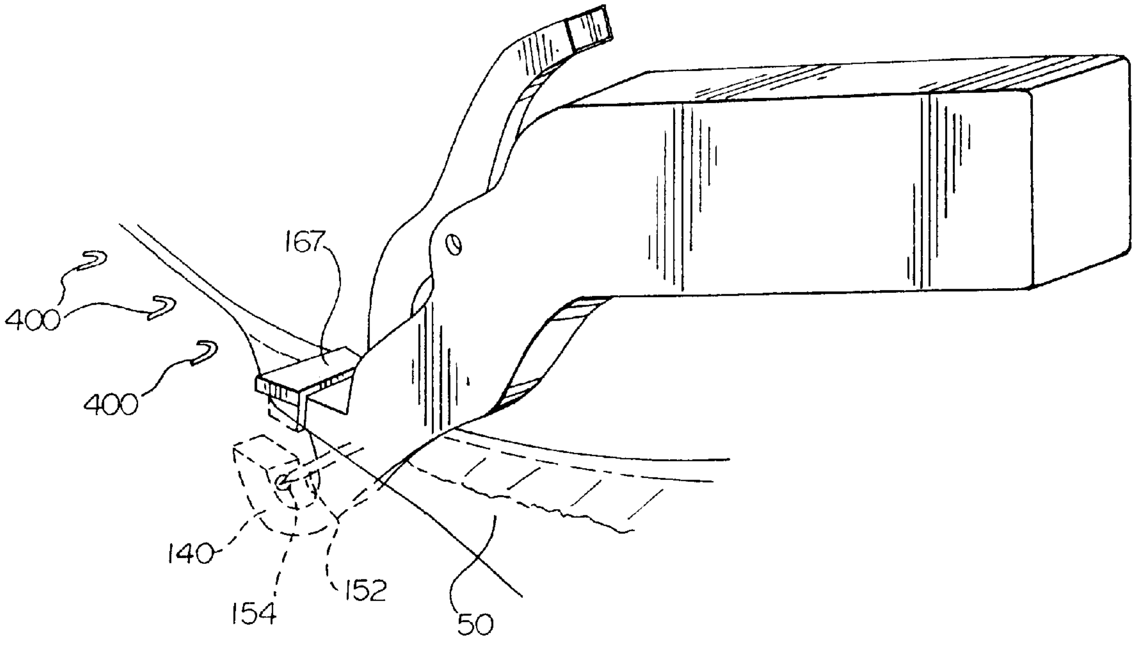
FIG. 37 is an isometric view of an alternate embodiment of the applicator assembly in which the fasteners are inserted obliquely into the tissue.

FIG. 37 shows another alternate embodiment of applicator assembly 100 in which the fasteners 400 are inserted obliquely into the tissue along the vertical interface 51. In this embodiment, the penetrating needles 152, 154 are oriented obliquely downward relative to the horizontal and the distance d1 on the driving head 140 is reduced. An upper projection 167 extends on top of the vertical interface 51 of the opening 50 to serve as a guide and the aperture 141 between upper projection 167 and the driving head 140 is positioned to require less rotational movement of the applicator assembly 100 in the plane of the vertical interface 51 when the tissue is being positioned in the driving head 140 or the applicator assembly 100 is being positioned for insertion of a subsequent fastener 400. One advantage of the oblique orientation of the fasteners 400 along the vertical interface 51 of opening 50 is that the effective spacing between backing members 408 of adjacent fasteners 400 is reduced, thereby affording the opportunity to increase the resulting holding pressure that can be applied across the vertical interface 51 to resist tearing by being able to insert more fasteners per longitudinal distance of the opening 50.

Figure 38:
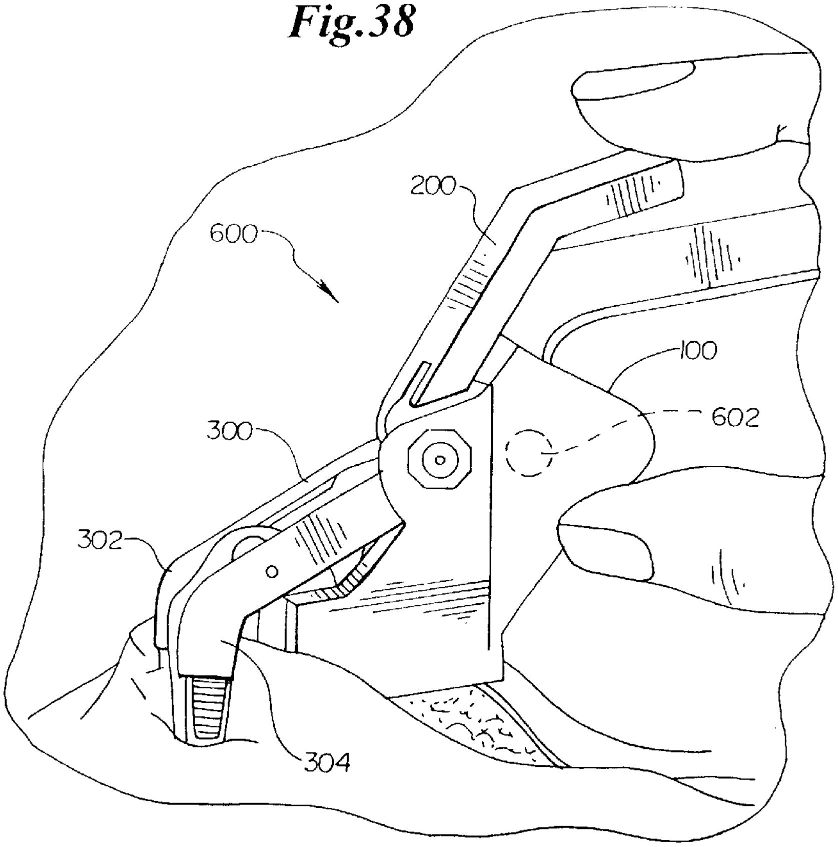
FIG. 38 is an isometric view of an alternate embodiment of the present invention in which the tissue manipulator and the applicator assembly are incorporated in a single hand-held instrument.

FIG. 38 shows another embodiment of the present invention in which the tissue manipulator 300 and the applicator assembly 100 are integrated together into a single handheld surgical instrument 600. In this embodiment, a manual trigger 200 is used to activate first the lateral compression operation of the arms 302, 304 of the tissue manipulator assembly 300 and then is further depressed to engage the delivery mechanism 128. A force translation mechanism 602 inside the handle 110 in the form of a cam, wedge or similar arrangement is first engaged by the depression of the trigger 200. Further depression of trigger 200 then causes delivery mechanism 128 to be actuated. It will be appreciated that a single handheld surgical instrument 600 integrating the structures of both the applicator assembly 100 and the tissue manipulator assembly 300 could be arranged and operated in a number of ways. For example, two trigger actuators could be used instead of one two-stage actuator. Instead of arranging the tissue manipulator assembly 300 and the applicator assembly 100 inline in the same orientation, the two assemblies 300 and 100 could be arranged to face each other in the longitudinal orientation.

Although the present invention has been described with respect to the various embodiments, it will be understood that numerous insubstantial changes in configuration, arrangement or appearance of the elements of the present invention can be made without departing from the intended scope of the present invention. Accordingly, it is intended that the scope of the present invention be determined by the claims as set forth.

What is claimed:

1. A mechanical method of bilaterally securing skin tissue with a fastener comprising:

approximating a portion of an interior surface of each of two pieces of living dermis tissue along a vertical interface that is generally perpendicular in at least one orientation to an exterior surface defined by epidermis tissue associated with the living dermis tissue without overlapping either interior surface across the vertical interface;

positioning a mechanical apparatus having a driving head portion positioned in the vertical interface and at least partially below the exterior surface and a handle portion positioned at least partially above the exterior surface; and utilizing the mechanical apparatus to bilaterally drive at least one portionof the fastener through each piece of the living dermis tissue behind the vertical interface and the interior surface of that piece of tissue such that the fastener is positioned below the exterior surface and a portion of the fastcner is positioned generally transverse to the vertical interface.

2. The method of claim 1, wherein the fastener includes at least two leg members and a cross-member and wherein the step of utilizing the mechanical apparatus simultaneously bilaterally drives each of the at least two leg members through a corresponding piece of the living dermis tissue.

3. The method of claim 2, wherein the cross-member is the portion of the fastener positioned generally transverse to the vertical interface and wherein the step of utilizing the mechanical apparatus positions a working plane of the fastener defined by the cross-member and two leg members in a horizontal orientation generally parallel in at least one orientation to the exterior surface defined by epidermis tissue.

4. The method of claim 1, wherein the fastener includes a portion configurable in a generally U-shaped configuration and wherein the step of utilizing the mechanical apparatus sequentially bilaterally drives the fastener first through one of the pieces of living dermis tissue and then through another of the pieces of living dermis tissue.

5. A mechanical method of bilateral fastening of opposing skin tissue across an opening comprising:

utilizilig a manipulator apparatus to position the opposing tissue together such that dermal layers are proximate each other at the opening and a pair of spaced apart target tissue zones are presented to a fastening apparatus, each target tissue zone being defined in a plane of each epidermal layer generally perpendicular to both a surface of the associated epidermal layer and a longitudinal orientation of the opening;

utilizing the fastening apparatus to bilaterally secure the dermal layers by inserting a fastener through each of the target tissue zones while opposing tissue is positioned together in an orientation generally perpendicular to the plane of the target tissue zones.

6. The method of claim 5, wherein each target tissue zone is defined in the plane by a rectangle of dimensions less than or equal to 2 mm deep by less than or equal to 20 mm wide on opposite sides of the longitudinal orientation of the opening and at least 0.1 mm below the surface of the associated epidermal layer.

7. The method of claim 6, wherein the rectangle has dimensions of 1 mm deep by 10 mm wide.

8. A mechanical method of fastening of a pair of opposing pieces of skin tissue across a gap comprising:

utilizing a mechanical apparatus to position a dermal layer of each of the opposing skin tissue together at the gap such that a pair of unique tissue target zones in the dermal layer are presented, each tissue target zone being defined in a three dimensional volume of one of the pieces of opposing skin tissue at a depth of between 0.1 mm and 2.0 mm below an exterior surface of the skin tissue, at a width of between 1 mm and 20 mm from an edge of the gap and along a longitudinal length of the gap wherein the depth and width define an insertion plane generally perpendicular to the longitudinal length of the gap;

utilizing a fastening apparatus to secure the dermal layers by inserting a portion of a fastener through the insertion plane into each tissue target zone while the opposing tissue is together with no portion of the fastener above the exterior surface of the skin tissue.

9. The method of claim 8, wherein the fastener is inserted in each tissue target zone in a generally horizontal orientation parallel to the exterior surface of the skin tissue.

10. The method of claim 8, wherein the fastener is inserted in each tissue target zone in a generally oblique orientation and parallel to the exterior surface of the skin tissue.

* * * * *

UNITED STATES PATENT AND TRADEMARK OFFICE

CERTIFICATE OF CORRECTION

PATENT NO. : 6,726,705 B2

DATED : April 27, 2004

INVENTOR(S) : James A. Peterson et al.

It is certified that error appears in the above-identified patent and that said Letters Patent is hereby corrected as shown below:

Title page,

Item [*] Notice, should read -- 96 days --.

Signed and Sealed this

Twenty-fifth Day of October, 2005

JON W. DUDAS

*Director of the United States Patent and Trademark Office*

UNITED STATES PATENT AND TRADEMARK OFFICE

CERTIFICATE OF CORRECTION

PATENT NO. : 6,726,705 B2
APPLICATION NO. : 10/179628
DATED : April 27, 2004
INVENTOR(S) : James A. Peterson et al.

It is certified that error appears in the above-identified patent and that said Letters Patent is hereby corrected as shown below:

Title Page, Column 1 (56) under Refer cited – Please add cited U.S. Patent reference --5,505,363, 4/1996 Green et al.--

Col. 1, line 57 – Please add ";" after 3,792,010.

Col. 5, line 36 – Please add "," after membranes.

Col. 7, line 59 – Please change "bore" to "bored".

Col. 15, line 46 – Please add a space between the words "portion" and "of"

Col. 16, line 18 – Please change "epidermal" to "dermal".

Signed and Sealed this

First Day of August, 2006

JON W. DUDAS
*Director of the United States Patent and Trademark Office*